United States Patent
Huo

(10) Patent No.: US 11,639,524 B2
(45) Date of Patent: May 2, 2023

(54) NORMALIZATION AND BASELINE SHIFT REMOVAL BY ROTATION IN ADDED DATA DIMENSIONS

(71) Applicant: Roche Sequencing Solutions, Inc., Pleasanton, CA (US)

(72) Inventor: Shouqin Huo, San Diego, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 399 days.

(21) Appl. No.: 16/883,843

(22) Filed: May 26, 2020

(65) Prior Publication Data

US 2020/0283844 A1 Sep. 10, 2020

Related U.S. Application Data

(63) Continuation of application No. PCT/US2018/062081, filed on Nov. 20, 2018.
(Continued)

(51) Int. Cl.
*G01N 33/487* (2006.01)
*G16B 40/10* (2019.01)
(Continued)

(52) U.S. Cl.
CPC ..... *C12Q 1/6869* (2013.01); *G01N 33/48721* (2013.01); *G16B 30/00* (2019.02);
(Continued)

(58) Field of Classification Search
None
See application file for complete search history.

(56) References Cited

U.S. PATENT DOCUMENTS

2014/0154790 A1 6/2014 Ono et al.
2014/0248608 A1 9/2014 Barrall et al.
(Continued)

FOREIGN PATENT DOCUMENTS

JP 2009-519705 A 5/2009
WO 2007057668 A1 5/2007
WO 2012/164679 A1 12/2012

OTHER PUBLICATIONS

Baumgartner, et al. ("A new approach to image segmentation with two-dimensional hidden Markov models." (Sep. 2013) BRICS Congress on Computational Intelligence and 11th Brazilian Congress on Computational Intelligence (pp. 213-222) (Year: 2013).*
(Continued)

*Primary Examiner* — Roy Y Yi
(74) *Attorney, Agent, or Firm* — Winston Chu

(57) ABSTRACT

A method of using a sequencing cell includes applying voltage across the sequencing cell, acquiring one or more signal values from the sequencing cell, and acquiring one or more correlated signal values that are correlated with respective values of the plurality of acquired signal values thereby forming a plurality of two-dimensional data points. The plurality of two-dimensional data points comprise values in a first dimension that equal the plurality of acquired signal value and values in a second dimension that equal the plurality of correlated signal values. The method can further include computing a plurality of transformed signal values by applying a two-dimensional transformation to the plurality of two-dimensional data points.

15 Claims, 21 Drawing Sheets

Related U.S. Application Data

(60) Provisional application No. 62/591,099, filed on Nov. 27, 2017.

(51) Int. Cl.
  *G16B 50/00*   (2019.01)
  *G01N 33/00*   (2006.01)
  *C12Q 1/6869*  (2018.01)
  *G16B 30/00*   (2019.01)

(52) U.S. Cl.
  CPC ............. *G16B 40/10* (2019.02); *G16B 50/00* (2019.02); *G01N 33/00* (2013.01)

(56) References Cited

U.S. PATENT DOCUMENTS

| | | |
|---|---|---|
| 2016/0178554 A1 | 6/2016 | Chen et al. |
| 2017/0089858 A1 | 3/2017 | Fernandez-Gomez et al. |
| 2017/0096703 A1* | 4/2017 | Dolan .................... G16B 40/00 |

OTHER PUBLICATIONS

International Search Report and Written Opinion dated Mar. 21, 2019 in corresponding PCT/US2018/062081 filed Nov. 20, 2018, pp. 1-12.

Kumar et al, PEG-Labeled Nucleotides and Nanopore Detection for Single Molecule DNA Sequencing by Synthesis, Scientific Reports, 2012, pp. 1-8, vol. 2.

Fuller, C. et al., Real-time single-molecule electronic DNA sequencing by synthesis using polymer-tagged nucleotides on a nanopore array, PNAS, (2016), pp. 5233-5238, vol. 113, No. 19.

* cited by examiner

NORMALIZATION AND BASELINE SHIFT REMOVAL BY ROTATION IN ADDED DATA DIMENSIONS

CROSS-REFERENCE TO RELATED APPLICATION

This application is a continuation of International Patent Application No. PCT/US2018/062081, filed Nov. 20, 2018, which claims the benefit of U.S. Provisional Patent Application No. 62/591,099, filed Nov. 27, 2017, the contents of which are incorporated by reference herein in their entirety.

BACKGROUND

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can exist. The size of the current is sensitive to the pore size and which molecule is in the nanopore. The molecule can be a particular tag attached to a particular nucleotide, thereby allowing detection of a nucleotide at a particular position of a nucleic acid. A voltage in a circuit including the nanopore can be measured (e.g., at an integrating capacitor) as a way of measuring the resistance of the molecule, thereby allowing detection of which molecule is in the nanopore.

A nanopore based sequencing chip may be used for DNA sequencing. A nanopore based sequencing chip can incorporate a large number of sensor cells configured as an array. For example, an array of one million cells may include 1000 rows by 1000 columns of cells.

The voltages that are measured can vary from chip to chip and from cell to cell of a same chip due to manufacturing variability. Therefore, it can be difficult to determine the correct molecule, which may be or correspond to the correct nucleotide in a particular nucleic acid or other polymer in a cell. In addition, other time dependent non-idealities in the measured voltages can lead to inaccuracies. And, because these circuits employ biochemical circuit elements, e.g., lipid bilayers, nanopores, etc., the variability in the electrical characteristics can be much higher than for traditional semiconductor circuits.

Accordingly, signal normalization techniques are desired to improve the accuracy and stability of sequencing processes.

BRIEF SUMMARY

Various embodiments provide techniques and systems related to the processing of output signals from cells of a multi-cell nanopore-based sequencing chip. An improved multi-cell nanopore-based sequencing chip may be built by employing various embodiments disclosed herein. For example, embodiments can include systems and methods for performing sequencing signal processing that can compensate for non-idealities in the sequencing signal that can be caused by, e.g., zero point voltage fluctuations/drift, gain drift, and baseline shift.

According to one embodiment, non-idealities in the sequencing signal can be compensated for by using an improved signal processing technique that can more effectively compensate for effects such as baseline-shift induced errors in the sequencing signal. The technique can include generating two-dimensional signal values, i.e., two-dimensional data points, from one dimensional bright mode signal values by associating each bright mode signal value with a corresponding correlated signal value. The two-dimensional data points can then be used to determine one or more two-dimensional transformations that can reduce a variance in the bright mode data. The technique can also include applying the two-dimensional transformation to newly acquired bright mode signal values to reduce a variance in the newly acquired bright mode signal values.

According to another embodiment, non-idealities in the sequencing signal can be compensated for by an improved signal processing system and method that employs a dark mode signal as a baseline that is subtracted from a bright mode signal. The dark mode signal is acquired during a "dark mode" period of an AC signal that when applied to the sequencing cell, a tag is pushed out of the barrel of the nanopore by the applied electric field. For example, to compensate for fluctuations in a zero point voltage of a cell, zero point compensated signal values can be computed by subtracting dark mode signal values from both the bright mode open channel signal values and the bright mode threaded signal values. The zero point compensated signal values may be used as input to other intermediate processing stages, e.g., stages that employ a running histogram and/or two-dimensional processing method as described below. The technique may correct the sequencing signal for errors induced by phenomena such as variation and/or drift in a cell's zero point voltage even if the value of the zero point voltage itself is unknown.

According to another embodiment, an improved estimate for a normalization factor can be determined using an improved signal processing technique. The technique can use a running/moving histogram to determine a an open-channel pore state (e.g., no tag in the pore) at any instant in time based on a set of historical measurements at that instant in time. The contributions to the histogram by the historical data can be controlled by weighting/discounting the historical data according to its age. A normalization factor for use in normalizing signals measured with a tag in the pore can be determined to be the sequencing signal value associated with the largest peak in the running/moving histogram.

The above techniques can be used independently or in any combination or order to improve the sequencing signal of a nanopore-based sequencing cell. One or more of the above techniques can also be applied on a cell-by-cell basis to improve the sequencing signal of a multi-cell nanopore-based sequencing chip.

Other embodiments are directed to systems and computer readable media associated with methods described herein.

A better understanding of the nature and advantages of embodiments of the present invention may be gained with reference to the following detailed description and the accompanying drawings.

TERMS

Figure 1:
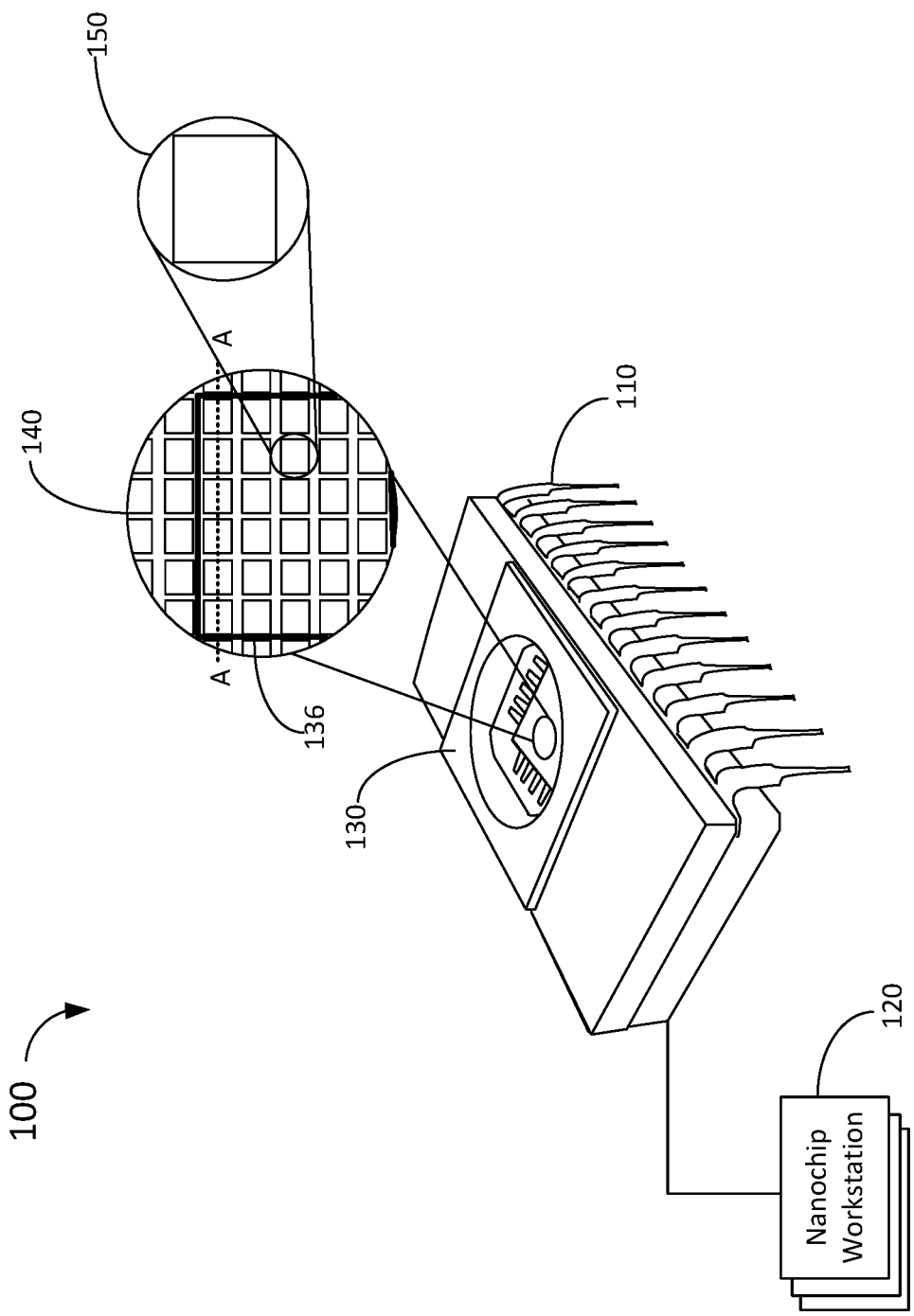
FIG. 1 is a top view of an embodiment of a nanopore sensor chip having an array of nanopore cells.

Unless defined otherwise, technical and scientific terms used herein have the same meaning as commonly understood by a person of ordinary skill in the art. Methods, devices, and materials similar or equivalent to those described herein can be used in the practice of disclosed techniques. The following terms are provided to facilitate understanding of certain terms used frequently and are not meant to limit the scope of the present disclosure. Abbreviations used herein have their conventional meaning within the chemical and biological arts.

A "nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid may be used interchangeably with gene, cDNA, mRNA, oligonucleotide, and polynucleotide.

The term "template" may refer to a single stranded nucleic acid molecule that is copied into a complementary strand of DNA nucleotides for DNA synthesis. In some cases, a template may refer to the sequence of DNA that is copied during the synthesis of mRNA.

The term "primer" may refer to a short nucleic acid sequence that provides a starting point for DNA synthesis. Enzymes that catalyze the DNA synthesis, such as DNA polymerases, can add new nucleotides to a primer for DNA replication.

A "polymerase" may refer to an enzyme that performs template-directed synthesis of polynucleotides. The term encompasses both a full length polypeptide and a domain that has polymerase activity. DNA polymerases are well-known to those skilled in the art, and include but are not limited to DNA polymerases isolated or derived from *Pyrococcus furiosus, Thermococcus litoralis*, and *Thermotoga maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

A "nanopore" refers to a pore, channel or passage formed or otherwise provided in a membrane. A membrane can be an organic membrane, such as a lipid bilayer, or a synthetic membrane, such as a membrane formed of a polymeric material. The nanopore can be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nanometers (nm) to about 1000 nm. In some implementations, a nanopore may be a protein.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

The term "tag" may refer to a detectable moiety that can be atoms or molecules, or a collection of atoms or molecules. A tag can provide an optical, electrochemical, magnetic, or electrostatic (e.g., inductive, capacitive) signature, which signature may be detected with the aid of a nanopore. Typically, when a nucleotide is attached to the tag it is called a "Tagged Nucleotide." The tag can be attached to the nucleotide via the phosphate moiety.

The term "bright period" may generally refer to the time period when a tag of a tagged nucleotide is forced into a nanopore by an electric field applied through an AC signal. The term "dark period" may generally refer to the time period when a tag of a tagged nucleotide is pushed out of the nanopore by the electric field applied through the AC signal. An AC cycle may include the bright period and the dark period. In different embodiments, the polarity of the voltage signal applied to a nanopore cell to put the nanopore cell into the bright period (or the dark period) may be different. The bright periods and the dark periods can correspond to different portions of an alternating signal relative to a reference voltage.

The term "signal value" may refer to a value of the sequencing signal output from a sequencing cell. According to certain embodiments, the sequencing signal may be an electrical signal that is measured and/or output from a point in a circuit of one or more sequencing cells e.g., the signal value may be (or represent) a voltage or a current. The signal value may represent the results of a direct measurement of voltage and/or current and/or may represent an indirect measurement, e.g., the signal value may be a measured duration of time for which it takes a voltage or current to reach a specified value. A signal value may represent any measurable quantity that correlates with the resistivity of a nanopore and from which the resistivity and/or conductance of the nanopore (threaded and/or unthreaded) may be derived. As another example, the signal value may correspond to a light intensity, e.g., from a fluorophore attached to a nucleotide being catalyzed to a nucleic acid with a polymerase.

The term "histogram" may refer to a data structure storing a count of a number of signal values for each of a specified number of intervals (bins). Each bin can correspond to a discrete value of a signal value (e.g., as determined by a resolution of an ADC) or to range of possible signal values within the interval.

DETAILED DESCRIPTION

According to certain embodiments, methods and systems disclosed herein relate to improvements in processing of a nanopore sequencing signal, e.g., a voltage signal as measured by an ADC connected to a nanopore cell. More specifically, methods and systems disclosed herein correct for both gain drift and baseline shift in a nanopore sequencing signal.

The phenomena of baseline shift in the nanopore sequencing signal can be related to charge imbalances that build up on certain inherently capacitive elements in the system (e.g., the working electrode of a cell) during the charging and discharging cycles that take place during the measurement process. Gain drift of the signal can be caused by relatively slow (hundreds or a thousand of seconds) changes in a membrane capacitance, where the membrane (e.g., a bilayer) covers the pore. Such membrane capacitance can change in a deterministic way, e.g., in response to physical changes in the bilayer.

A baseline drift of the signal can be removed (on a cell-by-cell basis) by a two-dimensional transformation, e.g., by rotating or flattening the cell's data in a 2-dimensional space, where one axis of the 2-dimensional space is defined to be the measured bright-channel voltage and the other axis is defined to be a derived value that serves as a proxy for the charge imbalance within the cell. In some embodiments, the proxy can be a time-weighted integrated history of either the bright-channel voltage or the dark-channel voltage. To compute the integrated history, historical voltage values can be summed together (i.e., integrated) with the contribution of older data to the sum being downgraded as the historical values age. The time constant for the temporal downgrading is related to the step-response time of the cell, which can be measured independently on a cell-by-cell basis.

A compensation of gain drift can be accomplished (on a cell-by-cell basis) through a point-by-point normalization of the cell's bright-channel signal. For example, to normalize the signal, each measured raw voltage can be divided by an estimate of the peak OC voltage. The estimate of the peak OC voltage can be found using what is referred to herein as a "moving histogram method." The peak OC voltage can be identified as the maximum value of the largest peak in a time-weighted running histogram of the data. For each point to be normalized, a histogram can be determined each time a new voltage is acquired, e.g., using an update procedure with the contribution of historical data to each new histogram being exponentially downgraded with age. The time constant for the exponential downgrade in the moving histogram method may be also related to rate at which the gain of the cell changes.

A compensation of a drift or fluctuation in a cell's zero point voltage $V_0$ can be accomplished by an improved processing technique that does not require measurement and tracking of $V_0$ explicitly. For example, by using the dark mode signal as a baseline signal that is subtracted from both the open channel signal and the threaded signal, the effect of $V_0$ drift on the sequencing signal can be compensated for. Furthermore, a variance in the raw sequencing signal values that is caused by a variance of $V_0$ is greatly reduced or even eliminated without needing to make any additional measurements to explicitly track $V_0$ for each cell during or before the sequencing operation.

I. Nanopore Sequencing Cell

Nanopore cells 150 in nanopore sensor chip 100 may be implemented in many different ways. For example, in some embodiments, tags of different sizes and/or chemical structures may be attached to different nucleotides in a nucleic acid molecule to be sequenced. In some embodiments, a complementary strand to a template of the nucleic acid molecule to be sequenced may be synthesized by hybridizing differently polymer-tagged nucleotides with the template. In some implementations, the nucleic acid molecule and the attached tags may both move through the nanopore, and an ion current passing through the nanopore may indicate the nucleotide that is in the nanopore because of the particular size and/or structure of the tag attached to the nucleotide. In some implementations, only the tags may be moved into the nanopore. There may also be many different ways to detect the different tags in the nanopores.

A. Nanopore Sequencing Cell Structure

Figure 2:
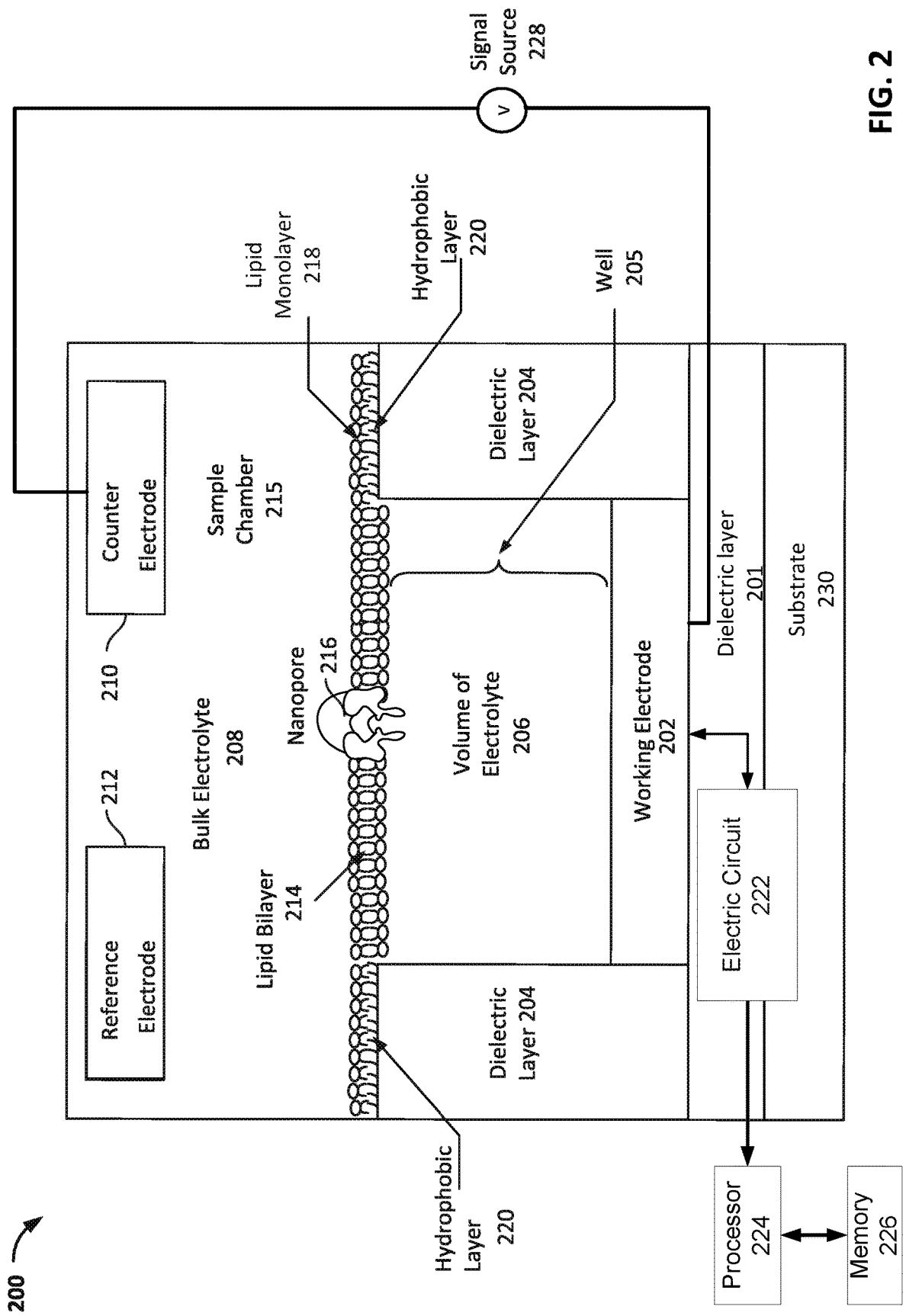
FIG. 2 illustrates an embodiment of a nanopore cell in a nanopore sensor chip that can be used to characterize a polynucleotide or a polypeptide.

FIG. 2 illustrates an embodiment of a nanopore cell 200 in a nanopore sensor chip, such as nanopore cell 150 in nanopore sensor chip 100 of FIG. 1, that can be used to characterize a polynucleotide or a polypeptide. Nanopore cell 200 may include a well 205 formed of dielectric layers 201 and 204; a membrane, such as a lipid bilayer 214 formed over well 205; and a sample chamber 215 on lipid bilayer 214 and separated from well 205 by lipid bilayer 214. Well 205 may contain a volume of electrolyte 206, and sample chamber 215 may hold bulk electrolyte 208 containing a nanopore, e.g., a soluble protein nanopore transmembrane molecular complexes (PNTMC), and the analyte of interest (e.g., a nucleic acid molecule to be sequenced).

Nanopore cell 200 may include a working electrode 202 at the bottom of well 205 and a counter electrode 210 disposed in sample chamber 215. A signal source 228 may apply a voltage signal between working electrode 202 and counter electrode 210. A single nanopore (e.g., a PNTMC) may be inserted into lipid bilayer 214 by an electroporation process caused by the voltage signal, thereby forming a nanopore 216 in lipid bilayer 214. The individual membranes (e.g., lipid bilayers 214 or other membrane structures) in the array may be neither chemically nor electrically connected to each other. Thus, each nanopore cell in the array may be an independent sequencing machine, producing data unique to the single polymer molecule associated with the nanopore that operates on the analyte of interest and modulates the ionic current through the otherwise impermeable lipid bilayer.

As shown in FIG. 2, nanopore cell 200 may be formed on a substrate 230, such as a silicon substrate. Dielectric layer 201 may be formed on substrate 230. Dielectric material used to form dielectric layer 201 may include, for example, glass, oxides, nitrides, and the like. An electric circuit 222 for controlling electrical stimulation and for processing the signal detected from nanopore cell 200 may be formed on substrate 230 and/or within dielectric layer 201. For example, a plurality of patterned metal layers (e.g., metal 1 to metal 6) may be formed in dielectric layer 201, and a plurality of active devices (e.g., transistors) may be fabricated on substrate 230. In some embodiments, signal source 228 is included as a part of electric circuit 222. Electric circuit 222 may include, for example, amplifiers, integrators, analog-to-digital converters, noise filters, feedback control logic, and/or various other components. Electric circuit 222 may be further coupled to a processor 224 that is coupled to a memory 226, where processor 224 can analyze the sequencing data to determine sequences of the polymer molecules that have been sequenced in the array.

Working electrode 202 may be formed on dielectric layer 201, and may form at least a part of the bottom of well 205. In some embodiments, working electrode 202 is a metal electrode. For non-faradaic conduction, working electrode 202 may be made of metals or other materials that are resistant to corrosion and oxidation, such as, for example, platinum, gold, titanium nitride, and graphite. For example, working electrode 202 may be a platinum electrode with electroplated platinum. In another example, working electrode 202 may be a titanium nitride (TiN) working electrode. Working electrode 202 may be porous, thereby increasing its surface area and a resulting capacitance associated with working electrode 202. Because the working electrode of a nanopore cell may be independent from the working electrode of another nanopore cell, the working electrode may be referred to as cell electrode in this disclosure.

Dielectric layer 204 may be formed above dielectric layer 201. Dielectric layer 204 forms the walls surrounding well 205. A dielectric material used to form dielectric layer 204 may include, for example, glass, oxide, silicon mononitride (SiN), polyimide, or other suitable hydrophobic insulating material. The top surface of dielectric layer 204 may be silanized. The silanization may form a hydrophobic layer 220 above the top surface of dielectric layer 204. In some embodiments, hydrophobic layer 220 has a thickness of about 1.5 nanometers (nm).

Well 205 formed by walls of the dielectric layer 204 includes volume of electrolyte 206 above working electrode 202. Volume of electrolyte 206 may be buffered and may include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$). In some embodiments, volume of electrolyte 206 has a thickness of about three microns ($\mu$m).

As also shown in FIG. 2, a membrane may be formed on top of dielectric layer 204 and span across well 205. In some embodiments, the membrane may include a lipid monolayer 218 formed on top of hydrophobic layer 220. As the membrane reaches the opening of well 205, lipid monolayer 218 may transition to lipid bilayer 214 that spans across the opening of well 205. The lipid bilayer may comprise or consist of phospholipid, for example, selected from diphytanoyl-phosphatidylcholine (DPhPC), 1,2-diphytanoyl-sn-glycero-3-phosphocholine, 1,2-Di-O-Phytanyl-sn-Glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy (polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy (polyethylene glycol)-2000]; 1,2-dioleoyl-sn-glycero-3-phosphoethanolamine-N-lactosyl; GM1 Ganglioside, Lysophosphatidylcholine (LPC) or any combination thereof.

As shown, lipid bilayer 214 is embedded with a single nanopore 216, e.g., formed by a single PNTMC. As described above, nanopore 216 may be formed by inserting a single PNTMC into lipid bilayer 214 by electroporation. Nanopore 216 may be large enough for passing at least a portion of the analyte of interest and/or small ions (e.g., $Na^+$, $K^+$, $Ca^{2+}$, $Cl^-$) between the two sides of lipid bilayer 214.

Sample chamber 215 is over lipid bilayer 214, and can hold a solution of the analyte of interest for characterization. The solution may be an aqueous solution containing bulk electrolyte 208 and buffered to an optimum ion concentration and maintained at an optimum pH to keep the nanopore 216 open. Nanopore 216 crosses lipid bilayer 214 and provides the only path for ionic flow from bulk electrolyte 208 to working electrode 202. In addition to nanopores (e.g., PNTMCs) and the analyte of interest, bulk electrolyte 208 may further include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

Counter electrode 210 may be an electrochemical potential sensor. In some embodiments, counter electrode 210 may be shared between a plurality of nanopore cells, and may therefore be referred to as a common electrode. In some cases, the common potential and the common electrode may be common to all nanopore cells, or at least all nanopore cells within a particular grouping. The common electrode can be configured to apply a common potential to the bulk electrolyte 208 in contact with the nanopore 216. Counter electrode 210 and working electrode 202 may be coupled to signal source 228 for providing electrical stimulus (e.g., voltage bias) across lipid bilayer 214, and may be used for sensing electrical characteristics of lipid bilayer 214 (e.g., resistance, capacitance, and ionic current flow). In some embodiments, nanopore cell 200 can also include a reference electrode 212.

In some embodiments, various checks can be made during creation of the nanopore cell as part of calibration. Once a nanopore cell is created, further calibration steps can be performed, e.g., to identify nanopore cells that are performing as desired (e.g., one nanopore in the cell). Such calibration checks can include physical checks, voltage calibration, open channel calibration, and identification of cells with a single nanopore.

B. Detection Signals of Nanopore Sequencing Cell

Nanopore cells in nanopore sensor chip, such as nanopore cells 150 in nanopore sensor chip 100, may enable parallel sequencing using a single molecule nanopore-based sequencing by synthesis (Nano-SBS) technique.

Figure 3:
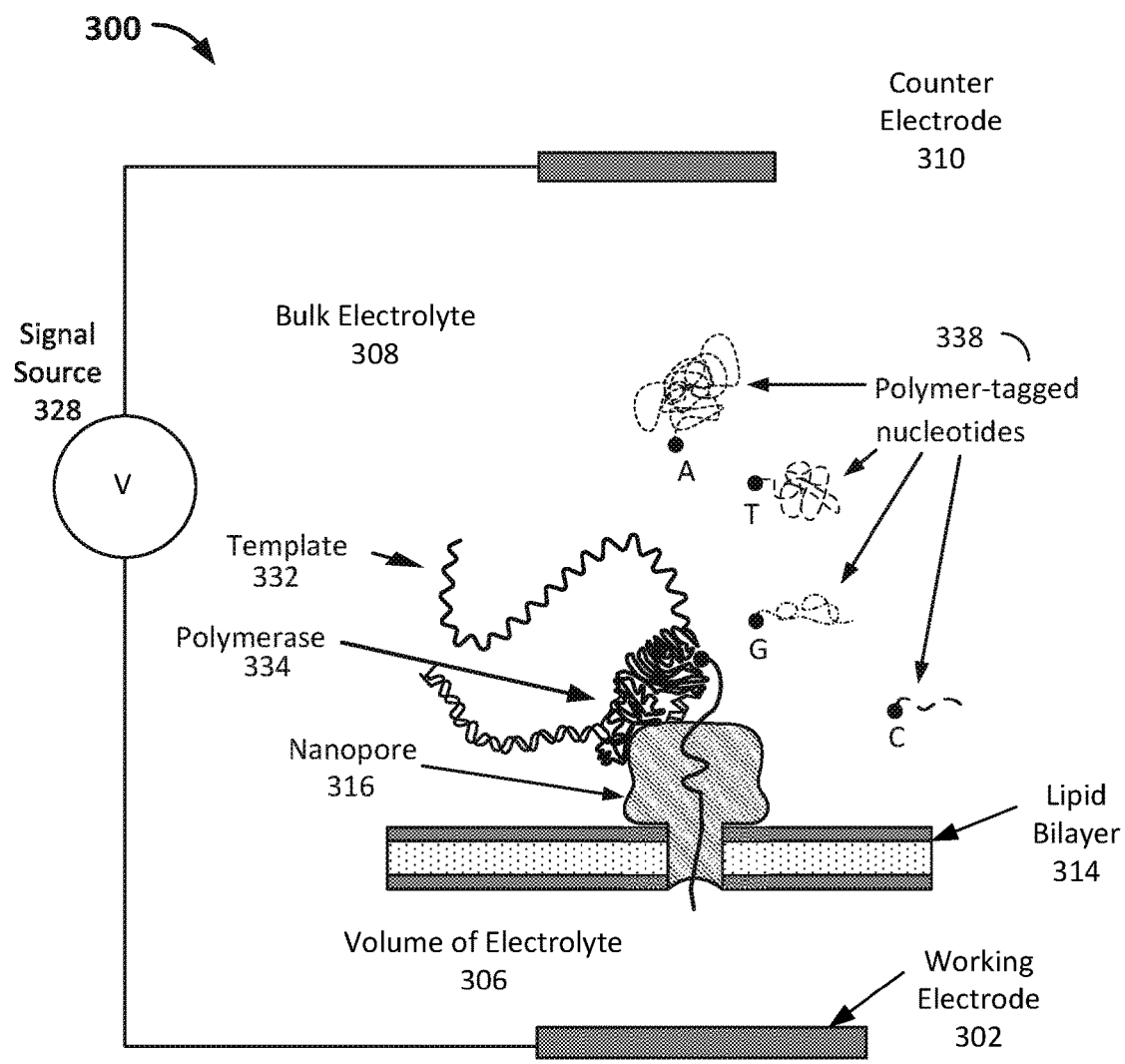
FIG. 3 illustrates an embodiment of a nanopore cell performing nucleotide sequencing using a nanopore-based sequencing-by-synthesis (Nano-SBS) technique.
Figure 3:
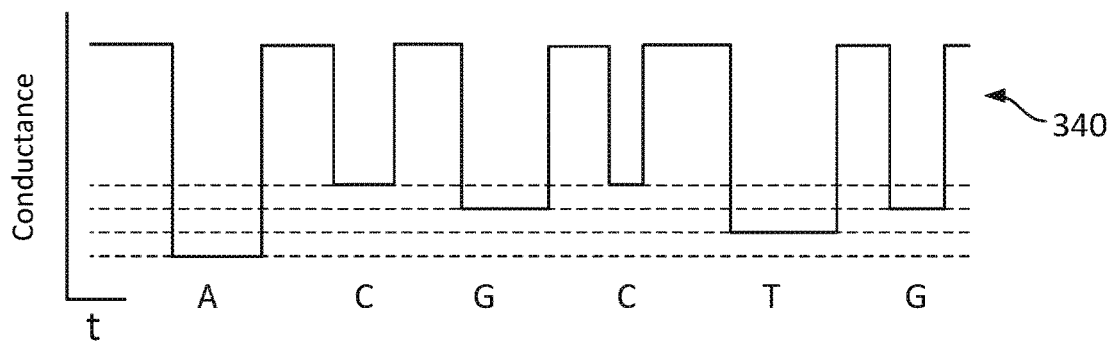

FIG. 3 illustrates an embodiment of a nanopore cell 300 performing nucleotide sequencing using the Nano-SBS technique. In the Nano-SBS technique, a template 332 to be sequenced (e.g., a nucleotide acid molecule or another analyte of interest) and a primer may be introduced into bulk electrolyte 308 in the sample chamber of nanopore cell 300. As examples, template 332 can be circular or linear. A nucleic acid primer may be hybridized to a portion of template 332 to which four differently polymer-tagged nucleotides 338 may be added.

In some embodiments, an enzyme (e.g., a polymerase 334, such as a DNA polymerase) may be associated with nanopore 316 for use in the synthesizing a complementary strand to template 332. For example, polymerase 334 may be covalently attached to nanopore 316. Polymerase 334 may catalyze the incorporation of nucleotides 338 onto the primer using a single stranded nucleic acid molecule as the template. Nucleotides 338 may comprise tag species ("tags") with the nucleotide being one of four different types: A, T, G, or C.

When a tagged nucleotide is correctly bound with polymerase 334, the tag may be pulled (loaded) into the nanopore by an electrical force, such as a force generated in the presence of an electric field generated by a voltage applied across lipid bilayer 314 and/or nanopore 316. The voltage may be applied using voltage source 328 that is connected to working electrode and counter electrode 310. The tail of the tag may be positioned in the barrel of nanopore 316. The tag held in the barrel of nanopore 316 may generate a unique ionic blockade signal 340 due to the tag's distinct chemical structure and/or size, thereby electronically identifying the added base to which the tag attaches.

As used herein, a "loaded" or "threaded" tag may be one that is positioned in and/or remains in or near the nanopore for an appreciable amount of time, e.g., 0.1 millisecond (ms) to 10,000 milliseconds. In some cases, a tag is loaded in the nanopore prior to being released from the nucleotide. In some instances, the probability of a loaded tag passing through (and/or being detected by) the nanopore after being released upon a nucleotide incorporation event is suitably high, e.g., 90% to 99%.

In some embodiments, before polymerase 334 is connected to nanopore 316, the conductance of nanopore 316 may be high, such as, for example, about 300 picosiemens (300 pS). As the tag is loaded in the nanopore, a unique conductance signal (e.g., signal 340) is generated due to the tag's distinct chemical structure and/or size. For example, the conductance of the nanopore can be about 60 pS, 80 pS, 100 pS, or 120 pS, each corresponding to one of the four types of tagged nucleotides. The polymerase may then undergo an isomerization and a transphosphorylation reaction to incorporate the nucleotide into the growing nucleic acid molecule and release the tag molecule.

In some cases, some of the tagged nucleotides may not match (complementary bases) with a current position of the nucleic acid molecule (template). The tagged nucleotides that are not base-paired with the nucleic acid molecule may also pass through the nanopore. These non-paired nucleotides can be rejected by the polymerase within a time scale that is shorter than the time scale for which correctly paired nucleotides remain associated with the polymerase. Tags bound to non-paired nucleotides may pass through the nanopore quickly, and be detected for a short period of time (e.g., less than 10 ms), while tags bounded to paired nucleotides can be loaded into the nanopore and detected for a long period of time (e.g., at least 10 ms). Therefore, non-paired nucleotides may be identified by a downstream processor based at least in part on the time for which the nucleotide is detected in the nanopore.

A conductance (or equivalently the resistance) of the nanopore including the loaded (threaded) tag can be measured via a current passing through the nanopore, thereby providing an identification of the tag species and thus the nucleotide at the current position. In some embodiments, a direct current (DC) signal can be applied to the nanopore cell (e.g., so that the direction at which the tag moves through the nanopore is not reversed). However, operating a nanopore sensor for long periods of time using a direct current can change the composition of the electrode, unbalance the ion concentrations across the nanopore, and have other undesirable effects that can affect the lifetime of the nanopore cell. Applying an alternating current (AC) waveform can reduce the electro-migration to avoid these undesirable effects and have certain advantages as described below. The nucleic acid sequencing methods described herein that utilize tagged nucleotides are fully compatible with applied AC voltages, and therefore an AC waveform can be used to achieve these advantages.

The ability to re-charge the electrode during the AC detection cycle can be advantageous when sacrificial electrodes, electrodes that change molecular character in the current-carrying reactions (e.g., electrodes comprising silver), or electrodes that change molecular character in current-carrying reactions are used. An electrode may deplete during a detection cycle when a direct current signal is used. The recharging can prevent the electrode from reaching a depletion limit, such as becoming fully depleted, which can be a problem when the electrodes are small (e.g., when the electrodes are small enough to provide an array of electrodes having at least 500 electrodes per square millimeter). Electrode lifetime in some cases scales with, and is at least partly dependent on, the width of the electrode.

Suitable conditions for measuring ionic currents passing through the nanopores are known in the art and examples are provided herein. The measurement may be carried out with a voltage applied across the membrane and pore. In some embodiments, the voltage used may range from −400 mV to +400 mV. The voltage used is preferably in a range having a lower limit selected from −400 mV, −300 mV, −200 mV, −150 mV, −100 mV, −50 mV, −20 mV, and 0 mV, and an upper limit independently selected from +10 mV, +20 mV, +50 mV, +100 mV, +150 mV, +200 mV, +300 mV, and +400 mV. The voltage used may be more preferably in the range of 100 mV to 240 mV and most preferably in the range of 160 mV to 240 mV. It is possible to increase discrimination between different nucleotides by a nanopore using an increased applied potential. Sequencing nucleic acids using AC waveforms and tagged nucleotides is described in US Patent Publication No. US 2014/0134616 entitled "Nucleic Acid Sequencing Using Tags," filed on Nov. 6, 2013, which is herein incorporated by reference in its entirety. In addition to the tagged nucleotides described in US 2014/0134616, sequencing can be performed using nucleotide analogs that lack a sugar or acyclic moiety, e.g., (S)-Glycerol nucleoside triphosphates (gNTPs) of the five common nucleobases: adenine, cytosine, guanine, uracil, and thymine (Horhota et al., Organic Letters, 8:5345-5347 [2006]).

C. Electric Circuit of Nanopore Sequencing Cell

Figure 4:
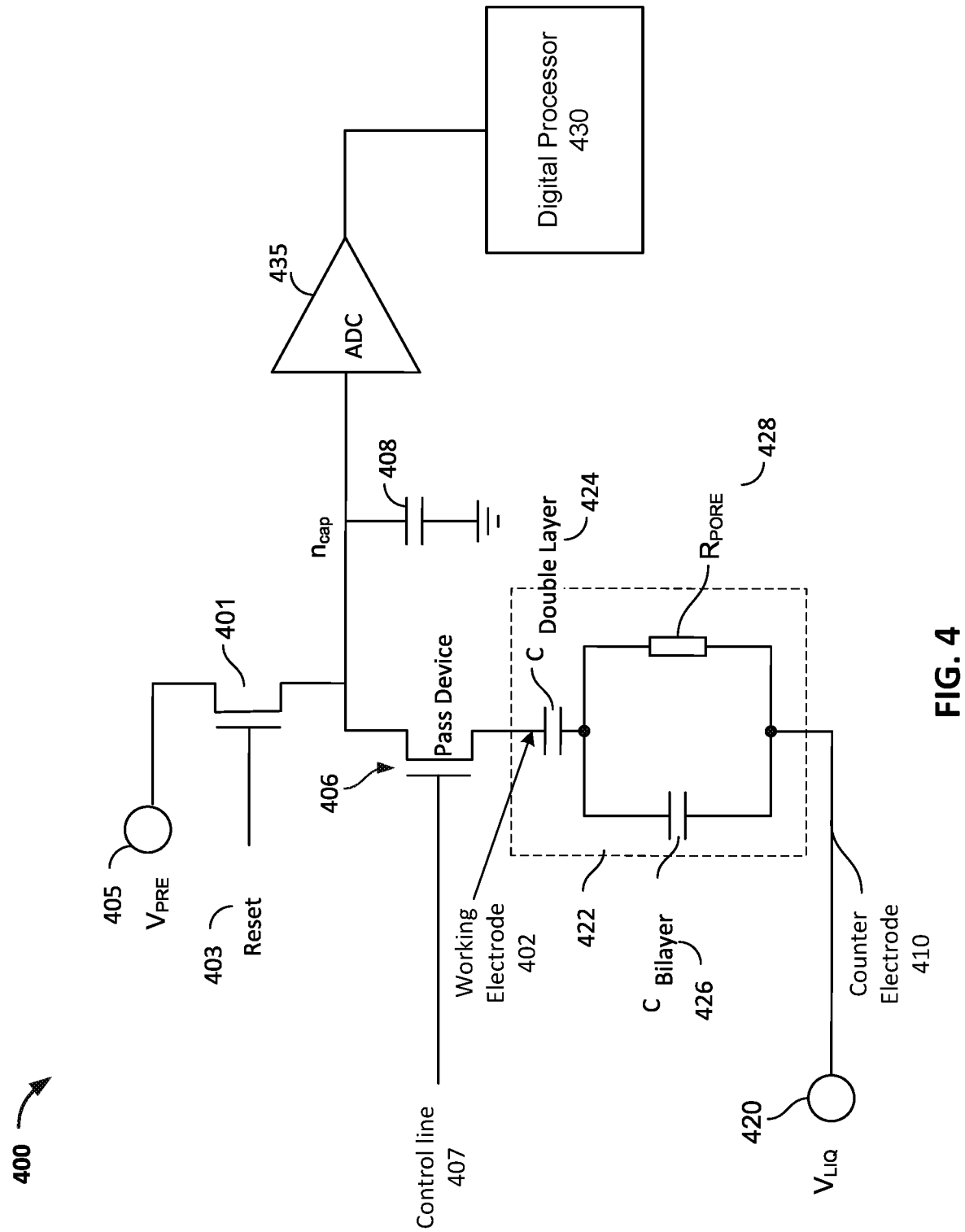
FIG. 4 illustrates an embodiment of an electric circuit in a nanopore cell.

FIG. 4 illustrates an embodiment of an electric circuit 400 (which may include portions of electric circuit 222 in FIG. 2) in a nanopore cell, such as nanopore cell 200. As described above, in some embodiments, electric circuit 400 includes a counter electrode 410 that may be shared between a plurality of nanopore cells or all nanopore cells in a nanopore sensor chip, and may therefore also be referred to as a common electrode. The common electrode can be configured to apply a common potential to the bulk electrolyte (e.g., bulk electrolyte 208) in contact with the lipid bilayer (e.g., lipid bilayer 214) in the nanopore cells by connecting to a voltage source $V_{LIQ}$ 420. In some embodiments, an AC non-Faradaic mode may be utilized to modulate voltage $V_{LIQ}$ with an AC signal (e.g., a square wave) and apply it to the bulk electrolyte in contact with the lipid bilayer in the nanopore cell. In some embodiments, $V_{LIQ}$ is a square wave with a magnitude of ±200-250 mV and a frequency between, for example, 25 and 400 Hz. The bulk electrolyte between counter electrode 410 and the lipid bilayer (e.g., lipid bilayer 214) may be modeled by a large capacitor (not shown), such as, for example, 100 µF or larger.

FIG. 4 also shows an electrical model 422 representing the electrical properties of a working electrode 402 (e.g., working electrode 202) and the lipid bilayer (e.g., lipid bilayer 214). Electrical model 422 includes a capacitor 426 ($C_{BiLayer}$) that models a capacitance associated with the lipid bilayer and a resistor 428 ($R_{PORE}$) that models a variable resistance associated with the nanopore, which can change based on the presence of a particular tag in the nanopore. Electrical model 422 also includes a capacitor 424 having a double layer capacitance ($C_{Double\ Layer}$) and representing the electrical properties of working electrode 402 and well 205. Working electrode 402 may be configured to apply a distinct potential independent from the working electrodes in other nanopore cells.

Pass device 406 is a switch that can be used to connect or disconnect the lipid bilayer and the working electrode from electric circuit 400. Pass device 406 may be controlled by control line 407 to enable or disable a voltage stimulus to be applied across the lipid bilayer in the nanopore cell. Before lipids are deposited to form the lipid bilayer, the impedance between the two electrodes may be very low because the well of the nanopore cell is not sealed, and therefore pass device 406 may be kept open to avoid a short-circuit condition. Pass device 406 may be closed after lipid solvent has been deposited to the nanopore cell to seal the well of the nanopore cell.

Circuit 400 may further include an on-chip integrating capacitor 408 ($n_{cap}$). Integrating capacitor 408 may be pre-charged by using a reset signal 403 to close switch 401, such that integrating capacitor 408 is connected to a voltage source $V_{PRE}$ 405. In some embodiments, voltage source $V_{PRE}$ 405 provides a constant reference voltage with a magnitude of, for example, 900 mV. When switch 401 is closed, integrating capacitor 408 may be pre-charged to the reference voltage level of voltage source $V_{PRE}$ 405.

After integrating capacitor 408 is pre-charged, reset signal 403 may be used to open switch 401 such that integrating capacitor 408 is disconnected from voltage source $V_{PRE}$ 405. At this point, depending on the level of voltage source $V_{LIQ}$, the potential of counter electrode 410 may be at a level higher than the potential of working electrode 402 (and integrating capacitor 408), or vice versa. For example, during a positive phase of a square wave from voltage source $V_{LIQ}$ (e.g., the bright or dark period of the AC voltage source signal cycle), the potential of counter electrode 410 is at a level higher than the potential of working electrode 402. During a negative phase of the square wave from voltage source $V_{LIQ}$ (e.g., the dark or bright period of the AC voltage source signal cycle), the potential of counter electrode 410 is at a level lower than the potential of working electrode 402. Thus, in some embodiments, integrating capacitor 408 may be further charged during the bright period from the pre-charged voltage level of voltage source $V_{PRE}$ 405 to a higher level, and discharged during the dark period to a lower level, due to the potential difference between counter electrode 410 and working electrode 402. In other embodiments, the charging and discharging may occur in dark periods and bright periods, respectively.

Integrating capacitor 408 may be charged or discharged for a fixed period of time, depending on the sampling rate of an analog-to-digital converter (ADC) 435, which may be higher than 1 kHz, 5 kHz, 10 kHz, 100 kHz, or more. For example, with a sampling rate of 1 kHz, integrating capacitor 408 may be charged/discharged for a period of about 1 ms, and then the voltage level may be sampled and converted by ADC 435 at the end of the integration period. A particular voltage level would correspond to a particular tag species in the nanopore, and thus correspond to the nucleotide at a current position on the template.

After being sampled by ADC 435, integrating capacitor 408 may be pre-charged again by using reset signal 403 to close switch 401, such that integrating capacitor 408 is connected to voltage source $V_{PRE}$ 405 again. The steps of pre-charging integrating capacitor 408, waiting for a fixed period of time for integrating capacitor 408 to charge or discharge, and sampling and converting the voltage level of integrating capacitor by ADC 435 can be repeated in cycles throughout the sequencing process.

A digital processor 430 can process the ADC output data, e.g., for normalization, data buffering, data filtering, data compression, data reduction, event extraction, or assembling ADC output data from the array of nanopore cells into various data frames. In some embodiments, digital processor 430 can perform further downstream processing, such as base determination. Digital processor 430 can be implemented as hardware (e.g., in a GPU, FPGA, ASIC, etc.) or as a combination of hardware and software.

Accordingly, the voltage signal applied across the nanopore can be used to detect particular states of the nanopore. One of the possible states of the nanopore is an open-channel state when a tag-attached polyphosphate is absent from the barrel of the nanopore, also referred to herein as the unthreaded state of the nanopore. Another four possible states of the nanopore each correspond to a state when one of the four different types of tag-attached polyphosphate nucleotides (A, T, G, or C) is held in the barrel of the nanopore. Yet another possible state of the nanopore is when the lipid bilayer is ruptured.

When the voltage level on integrating capacitor 408 is measured after a fixed period of time, the different states of a nanopore may result in measurements of different voltage levels. This is because the rate of the voltage decay (decrease by discharging or increase by charging) on integrating capacitor 408 (i.e., the steepness of the slope of a voltage on integrating capacitor 408 versus time plot) depends on the nanopore resistance (e.g., the resistance of resistor $R_{PORE}$ 428). More particularly, as the resistance associated with the nanopore in different states is different due to the molecules' (tags') distinct chemical structures, different corresponding rates of voltage decay may be observed and may be used to identify the different states of the nanopore. The voltage decay curve may be an exponential curve with an RC time constant $\tau = RC$, where R is the resistance associated with the nanopore (i.e., $R_{PORE}$ 428) and C is the capacitance associated with the membrane (i.e., capacitor 426 ($C_{Bilayer}$)) in parallel with R. A time constant of the nanopore cell can be, for example, about 200-500 ms. The decay curve may not fit exactly to an exponential curve due to the detailed implementation of the bilayer, but the decay curve may be similar to an exponential curve and is monotonic, thus allowing detection of tags.

In some embodiments, the resistance associated with the nanopore in an open-channel state may be in the range of 100 MΩ to 20 GΩ. In some embodiments, the resistance associated with the nanopore in a state where a tag is inside the barrel of the nanopore may be within the range of 200 MΩ to 40 GΩ. In other embodiments, integrating capacitor 408 may be omitted, as the voltage leading to ADC 435 will still vary due to the voltage decay in electrical model 422.

The rate of the decay of the voltage on integrating capacitor 408 may be determined in different ways. As explained above, the rate of the voltage decay may be determined by measuring a voltage decay during a fixed time interval. For example, the voltage on integrating capacitor 408 may be first measured by ADC 435 at time t1, and then the voltage is measured again by ADC 435 at time t2. The voltage difference is greater when the slope of the voltage on integrating capacitor 408 versus time curve is steeper, and the voltage difference is smaller when the slope of the voltage curve is less steep. Thus, the voltage difference may be used as a metric for determining the rate of the decay of the voltage on integrating capacitor 408, and thus the state of the nanopore cell.

In other embodiments, the rate of the voltage decay can be determined by measuring a time duration that is required for a selected amount of voltage decay. For example, the time required for the voltage to drop or increase from a first voltage level V1 to a second voltage level V2 may be measured. The time required is less when the slope of the voltage vs. time curve is steeper, and the time required is greater when the slope of the voltage vs. time curve is less steep. Thus, the measured time required may be used as a metric for determining the rate of the decay of the voltage on integrating capacitor $n_{cap}$ 408, and thus the state of the nanopore cell. One skilled in the art will appreciate the various circuits that can be used to measure the resistance of the nanopore, e.g., including current measurement techniques.

In some embodiments, electric circuit 400 may not include a pass device (e.g., pass device 406) and an extra capacitor (e.g., integrating capacitor 408 ($n_{cap}$)) that are fabricated on-chip, thereby facilitating the reduction in size of the nanopore-based sequencing chip. Due to the thin nature of the membrane (lipid bilayer), the capacitance associated with the membrane (e.g., capacitor 426 ($C_{Bilayer}$)) alone can suffice to create the required RC time constant without the need for additional on-chip capacitance. Therefore, capacitor 426 may be used as the integrating capacitor, and may be pre-charged by the voltage signal $V_{PRE}$ and subsequently be discharged or charged by the voltage signal $V_{LIQ}$. The elimination of the extra capacitor and the pass device that are otherwise fabricated on-chip in the electric circuit can significantly reduce the footprint of a single nanopore cell in the nanopore sequencing chip, thereby facilitating the scaling of the nanopore sequencing chip to include more and more cells (e.g., having millions of cells in a nanopore sequencing chip).

D. Data Sampling in Nanopore Cell

To perform sequencing of a nucleic acid, the voltage level of integrating capacitor (e.g., integrating capacitor 408 ($n_{cap}$) or capacitor 426 ($C_{Bilayer}$)) can be sampled and converted by the ADC (e.g., ADC 435) while a tagged nucleotide is being added to the nucleic acid. The tag of the nucleotide can be pushed into the barrel of the nanopore by the electric field across the nanopore that is applied through the counter electrode and the working electrode, for example, when the applied voltage is such that $V_{LIQ}$ is lower than $V_{PRE}$.

1. Threading

A threading event is when a tagged nucleotide is attached to the template (e.g., nucleic acid fragment), and the tag goes in and out of the barrel of the nanopore. This can happen multiple times during a threading event. When the tag is in the barrel of the nanopore, the resistance of the nanopore may be higher, and a lower current may flow through the nanopore.

During sequencing, a tag may not be in the nanopore in some AC cycles (referred to as an open-channel state), where the current is the highest because of the lower resistance of the nanopore. When a tag is attracted into the barrel of the nanopore, the nanopore is in a bright mode. When the tag is pushed out of the barrel of the nanopore, the nanopore is in a dark mode.

2. Bright and Dark Period

During an AC cycle, the voltage on integrating capacitor may be sampled multiple times by the ADC. For example, in one embodiment, an AC voltage signal is applied across the system at, e.g., about 100 Hz, and an acquisition rate of the ADC can be about 2000 Hz per cell. Thus, there can be about 20 data points (voltage measurements) captured per AC cycle (cycle of an AC waveform). Data points corresponding to one cycle of the AC waveform may be referred to as a set. In a set of data points for an AC cycle, there may be a subset captured when, for example, $V_{LIQ}$ is lower than $V_{PRE}$, which may correspond to a bright mode (period) where the tag is forced into the barrel of the nanopore. Another subset may correspond to a dark mode (period) where the tag is pushed out of the barrel of the nanopore by the applied electric field when, for example, $V_{LIQ}$ is higher than $V_{PRE}$.

3. Measured Voltages

For each data point, when the switch 401 is opened, the voltage at the integrating capacitor (e.g., integrating capacitor 408 ($n_{cap}$) or capacitor 426 ($C_{Bilayer}$)) will change in a decaying manner as a result of the charging/discharging by $V_{LIQ}$, e.g., as an increase from $V_{PRE}$ to $V_{LIQ}$ when $V_{LIQ}$ is higher than $V_{PRE}$ or a decrease from $V_{PRE}$ to $V_{LIQ}$ when $V_{LIQ}$ is lower than $V_{PRE}$. The final voltage values may deviate from $V_{LIQ}$ as the working electrode charges. The rate of change of the voltage level on the integrating capacitor may be governed by the value of the resistance of the bilayer, which may include the nanopore, which may in turn include a molecule (e.g., a tag of a tagged nucleotide) in the nanopore. The voltage level can be measured at a predetermined time after switch 401 opens.

Switch 401 may operate at the rate of data acquisition. Switch 401 may be closed for a relatively short time period between two acquisitions of data, typically right after a measurement by the ADC. The switch allows multiple data points to be collected during each sub-period (bright or dark) of each AC cycle of $V_{LIQ}$. If switch 401 remains open, the voltage level on the integrating capacitor, and thus the output value of the ADC, would fully decay and stay there. Instead, when switch 401 is closed, the integrating capacitor is pre-charged again (to $V_{PRE}$) and becomes ready for another measurement. Thus, switch 401 allows multiple data points to be collected for each sub-period (bright or dark) of each AC cycle. Such multiple measurements can allow higher resolution with a fixed ADC (e.g. 8-bit to 14-bit due to the greater number of measurements, which may be averaged). The multiple measurements can also provide kinetic information about the molecule threaded into the nanopore. The timing information may allow the determination of how long a threading takes place. This can also be used in helping to determine whether multiple nucleotides that are added to the nucleic acid strand are being sequenced.

Figure 5:
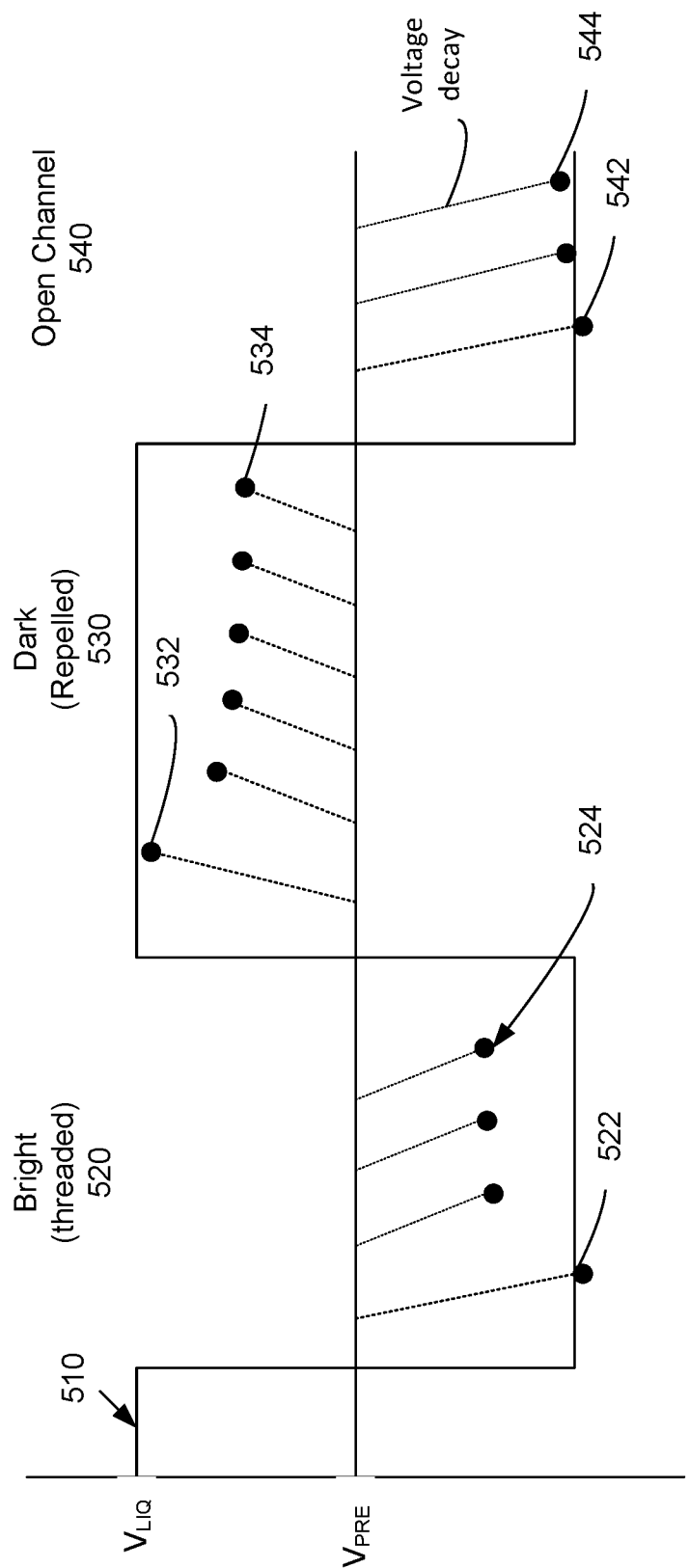
FIG. 5 shows example data points captured from a nanopore cell during bright periods and dark periods of AC cycles.

FIG. 5 shows example data points captured from a nanopore cell during bright periods and dark periods of AC cycles. In FIG. 5, the change in the data points is exaggerated for illustration purpose. The voltage ($V_{PRE}$) applied to the working electrode or the integrating capacitor is at a constant level, such as, for example, 900 mV. A voltage signal 510 ($V_{LIQ}$) applied to the counter electrode of the nanopore cells is an AC signal shown as a rectangular wave, where the duty cycle may be any suitable value, such as less than or equal to 50%, for example, about 40%.

During a bright period 520, voltage signal 510 ($V_{LIQ}$) applied to the counter electrode is lower than the voltage $V_{PRE}$ applied to the working electrode, such that a tag may be forced into the barrel of the nanopore by the electric field caused by the different voltage levels applied at the working electrode and the counter electrode (e.g., due to the charge on the tag and/or flow of the ions). When switch 401 is opened, the voltage at a node before the ADC (e.g., at an integrating capacitor) will decrease. After a voltage data point is captured (e.g., after a specified time period), switch 401 may be closed and the voltage at the measurement node will increase back to $V_{PRE}$ again. The process can repeat to measure multiple voltage data points. In this way, multiple data points may be captured during the bright period.

As shown in FIG. 5, a first data point 522 (also referred to as first point delta (FPD)) in the bright period after a change in the sign of the $V_{LIQ}$ signal may be lower than subsequent data points 524. This may be because there is no tag in the nanopore (open channel), and thus it has a low resistance and a high discharge rate. In some instances, first data point 522 may exceed the $V_{LIQ}$ level as shown in FIG. 5. This may be caused by the capacitance of the bilayer coupling the signal to the on-chip capacitor. Data points 524 may be captured after a threading event has occurred, i.e., a tag is forced into the barrel of the nanopore, where the resistance of the nanopore and thus the rate of discharging of the integrating capacitor depends on the particular type of tag that is forced into the barrel of the nanopore. Data points 524 may decrease slightly for each measurement due to charge built up at $C_{Double\ Layer}$ 424, as mentioned below.

During a dark period 530, voltage signal 510 ($V_{LIQ}$) applied to the counter electrode is higher than the voltage ($V_{PRE}$) applied to the working electrode, such that any tag would be pushed out of the barrel of the nanopore. When switch 401 is opened, the voltage at the measurement node increases because the voltage level of voltage signal 510 ($V_{LIQ}$) is higher than $V_{PRE}$. After a voltage data point is captured (e.g., after a specified time period), switch 401 may be closed and the voltage at the measurement node will decrease back to $V_{PRE}$ again. The process can repeat to measure multiple voltage data points. Thus, multiple data points may be captured during the dark period, including a first point delta 532 and subsequent data points 534. As described above, during the dark period, any nucleotide tag is pushed out of the nanopore, and thus minimal information about any nucleotide tag is obtained, besides for use in normalization.

FIG. 5 also shows that during bright period 540, even though voltage signal 510 ($V_{LIQ}$) applied to the counter electrode is lower than the voltage ($V_{PRE}$) applied to the working electrode, no threading event occurs (open-channel). Thus, the resistance of the nanopore is low, and the rate of discharging of the integrating capacitor is high. As a result, the captured data points, including a first data point 542 and subsequent data points 544, show low voltage levels.

The voltage measured during a bright or dark period might be expected to be about the same for each measurement of a constant resistance of the nanopore (e.g., made during a bright mode of a given AC cycle while one tag is in the nanopore), but this may not be the case when charge builds up at double layer capacitor 424 ($C_{Double\ Layer}$). This charge build-up can cause the time constant of the nanopore cell to become longer. As a result, the voltage level may be shifted, thereby causing the measured value to decrease for each data point in a cycle. Thus, within a cycle, the data points may change somewhat from data point to another data point, as shown in FIG. 5.

Further details regarding measurements can be found in, for example, U.S. Patent Publication No. 2016/0178577 entitled "Nanopore-Based Sequencing With Varying Voltage Stimulus," U.S. Patent Publication No. 2016/0178554 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation," the disclosures of which are incorporated by reference in their entirety for all purposes.

4. Normalization and Base Calling

For each usable nanopore cell of the nanopore sensor chip, a production mode can be run to sequence nucleic acids. The ADC output data captured during the sequencing can be normalized to provide greater accuracy. Normalization can account for offset effects, such as cycle shape, gain drift, charge injection offset, and baseline shift. In some implementations, the signal values of a bright period cycle corresponding to a threading event can be flattened so that a single signal value is obtained for the cycle (e.g., an average) or adjustments can be made to the measured signal to reduce the intra-cycle decay (a type of cycle shape effect). Gain drift generally scales entire signal and changes on the order to hundreds to thousands of seconds. As examples, gain drift can be triggered by changes in solution (pore resistance) or changes in bilayer capacitance. The baseline shift occurs with a timescale of ~100 ms, and relates to a voltage offset at the working electrode. The baseline shift can be driven by changes in an effective rectification ratio from threading as a result of a need to maintain charge balance in the sequencing cell from the bright period to the dark period.

After normalization, embodiments can determine clusters of voltages for the threaded channels, where each cluster corresponds to a different tag species, and thus a different nucleotide. The clusters can be used to determine probabilities of a given voltage corresponding to a given nucleotide. As another example, the clusters can be used to determine cutoff voltages for discriminating between different nucleotides (bases).

Example methods of determining bases of a nucleic acid based on signal measurements are provided below. Although the examples may use voltage measurements for illustration, the example techniques equally apply to other signal measurements, such as current measurements.

II. Sources of Error

Once the usable cells of a chip are identified, a production mode can be run to sequence nucleic acids, e.g., each cell sequencing one nucleic acid. The signal values measured during sequencing can be normalized to provide greater accuracy. For instance, the voltage level data that is acquired during a bright period of the AC drive voltage (referred to herein as the "bright mode voltages" or alternatively as the "bright period voltage") can be normalized. For example, the bright mode voltages can be normalized by dividing each measured bright mode data point by the bright mode voltage of the cell when the nanopore is in an unthreaded state, referred to herein as the "open channel voltage" or "bright mode open-channel voltage." By normalizing the bright mode voltage level data, the dynamic range of the raw ADC measurements is rescaled to a normalized range, generally to provide a range between 0 and 1, although values greater than 1 are possible, depending on the specific value used for bright mode open-channel voltage.

Normalization can allow compensating for changes to the system, e.g., changes in the electrical properties of a sequencing cell. For instance, the capacitances of circuit 400 may change over time. For example, the capacitance of capacitor 426 ($C_{Bilayer}$) can change because of physical changes in the bilayer area or thickness, e.g., at the edges of a well, where such change is referred to as gain drift. As another example, charge can build up in the cell as a result of differences in charge transfer between bright periods and dark periods, which is referred to as baseline shift (and sometimes fast baseline shift). A slow baseline shift can be caused by variability in the measurements circuit and changes in the electrical properties of the bilayer membrane. These examples are described in more detail below.

Such changes can affect the values measured for the exact same state, thereby causing instabilities. However, normalization can compensate for such changes to provide normalized values (e.g., voltages or currents) that are stable over time, thereby allowing greater accuracy in determining the sequence of a nucleic acid.

A. Idealized Normalization

Figure 6A:
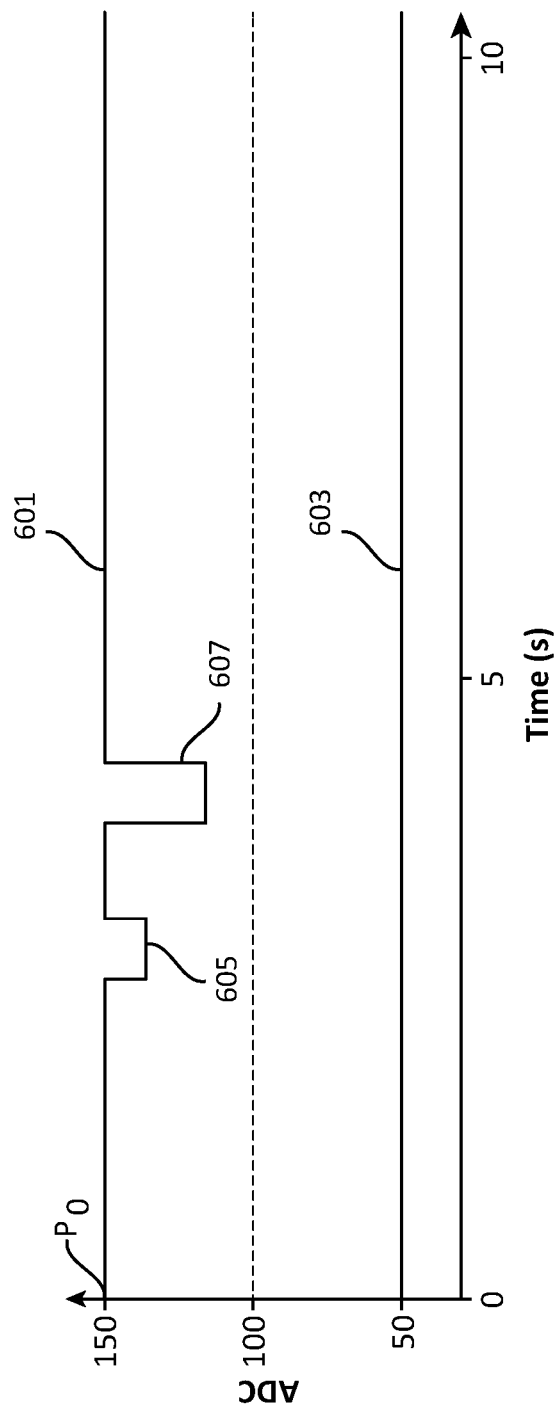
FIGS. 6A-6B illustrate the concept of normalization for an idealized ADC signal according to some embodiments.
Figure 6B:
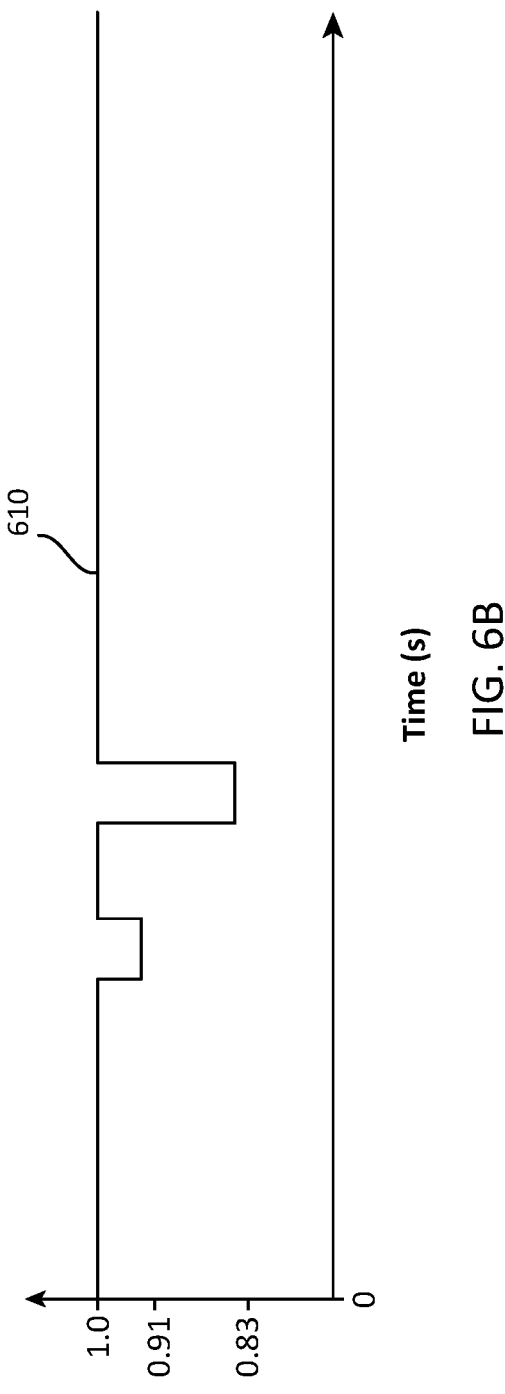

FIGS. 6A-6B illustrate the concept of normalization for an idealized ADC signal according to some embodiments. FIG. 6A shows idealized bright mode data 601 and idealized dark mode data 603 as might be measured by an ADC during a sequencing operation, e.g., as described above. The idealized ADC data of FIGS. 6A-6B is also shown on a much longer timescale than, e.g., the data described above in reference to FIG. 5. As such, the individual AC cycles are not visible in FIG. 5. Nevertheless, it should be understood that bright mode data 601 and dark mode data 603 are acquired during different half cycles of the AC drive voltage $V_{liq}$. Furthermore, the data shown in FIG. 6A are idealized in the sense that no noise, gain drift, and/or baseline shift is present, i.e., the open channel voltages (both bright mode and dark mode) are constant over an individual AC cycle as well as constant over time.

In addition, bright mode data 601 shows threading events 605 and 607 that correspond to two separate hypothetical threading events of two different tagged nucleotides. The measured voltages at threading events 605 and 607 are different due to the different tagged nucleotides being threaded. As shown here, the threading events occur over several AC cycles and occur on a fast enough timescale that during the threading events, no bright mode open-channel signal is measured. In some embodiments, one or more of threading events 605 and 607 could cause an increase in ADC values as opposed to a decrease. Such values can be referred to as above open channel.

In FIG. 6A, the open channel ADC value for the bright mode is represented by $P_0$, which may be used to normalize the ADC values for threading events 605 and 607. This normalization factor $P_0$ in this idealized example is constant at the measured value at t=0, which is 150 ADC values in this example. To perform the normalization in this case, all of the bright mode data can be divided by the same constant: $P_0=150$. For ease of description, the example of normalization by division is used throughout disclosure; however, one of ordinary skill will understand that multiplication by the inverse is mathematically equivalent, and thus may also be used without departing from the scope of the present disclosure.

FIG. 6B shows the normalized bright mode data 610 resulting from normalizing the idealized bright mode data 601 of FIG. 6A. In the normalized bright mode data, the open-channel level and the tag levels are not the raw ADC values, but rather span the range from 0 to 1. Because the bright mode open channel voltage is constant in this case, the normalization factor $P_0$ can be used to normalize the entire signal across the entire duration of the sequencing run. However, real signals suffer from a number of non-idealities that make this simple, single-valued normalization inaccurate. Two primary causes of errors in real sequencing systems are baseline shift and gain drift.

B. Gain Drift

Each sequencing cell has a voltage gain that depends on the lipid bi-layer capacitance. The gain corresponds to the voltage difference that is achieved between the two electrodes (e.g., counter electrode 210 and working electrode 202). For example, given the equation of $C=q/V$ for a capacitor, as the capacitance increases, the voltage would decrease when a same amount of charge is present. Accordingly, if the lipid bi-layer capacitance changes over time, then the voltage gain changes over time. If the voltage gain changes over time, then the bright mode and dark mode (both open channel and threaded) can change over time. In any real system, the bilayer capacitance may change over time, e.g., as the bilayer deforms. Such changes typically occur on the timescale of hundreds or thousands of seconds and, though slower than a typical threading event, still should be accounted for if high accuracy measurements are desired.

Figure 7:
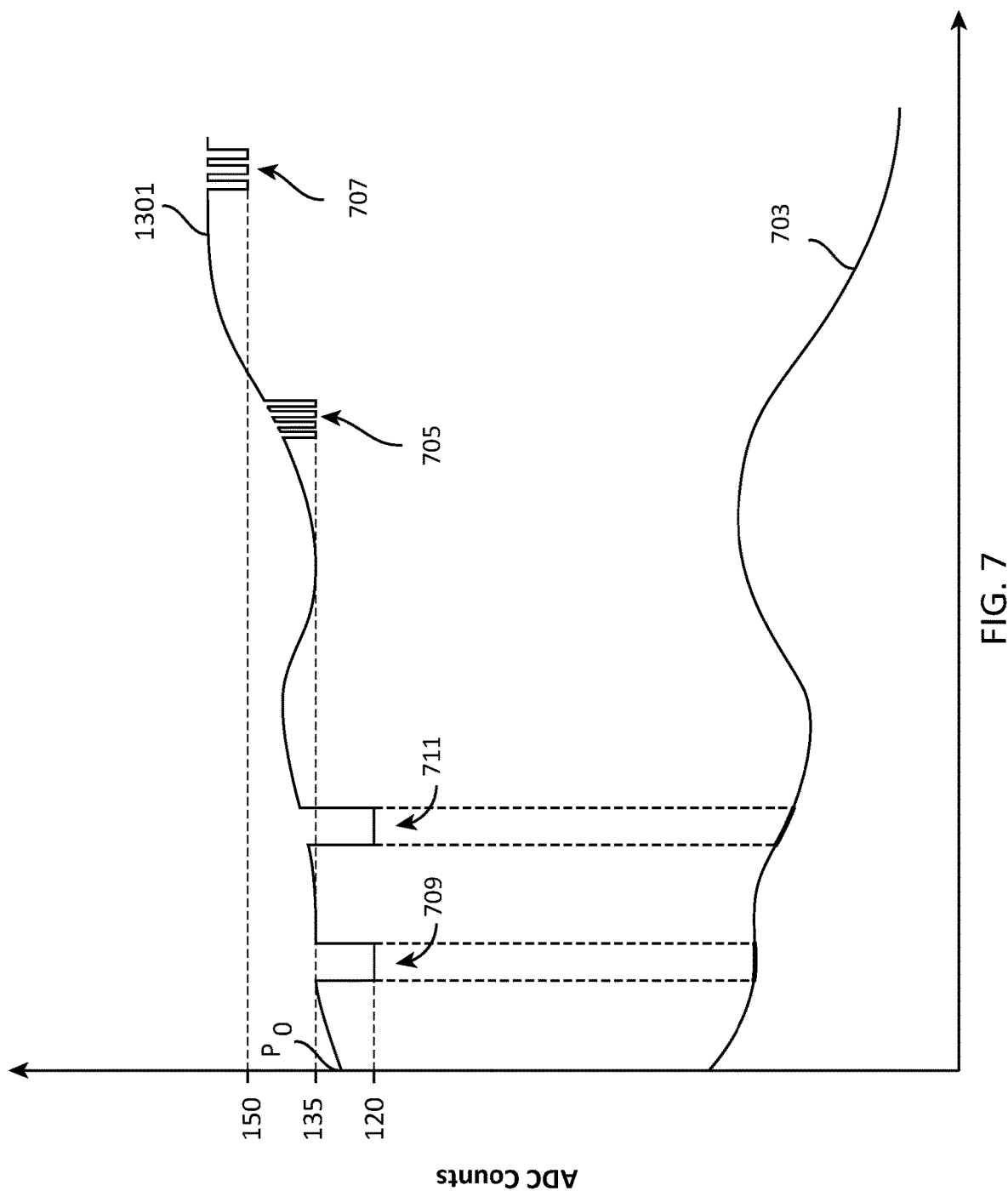
FIG. 7 shows an idealized signal that suffers from gain drift according to certain embodiments.

FIG. 7 shows an idealized signal that suffers from gain drift (with non-realistic timescales for both threading events and non-realistic gain drift to allow for both phenomena to be clearly shown on the same graph). Like FIGS. 6A-6B, FIG. 7 shows an idealized bright mode data 701 and idealized dark mode data 703 as would be measured by an ADC during a sequencing operation. The gain drift is illustrated as the overall drift in the open channel voltages for both bright and dark modes, with the drift being anti-correlated between bright and dark modes (e.g., when the bright mode increases, the dark mode decreases and vice versa). For the sake of clarifying the effect that gain drift has on measured ADC level of the same tag over time, 4 threading events are also shown, with each threading event involving the same species of tag, resulting in a same drop in voltage from the current open channel voltage. However, despite the fact that the same tag is being threaded during each event, the ADC value of this tag drifts over time. Thus, it could be the case that for this cell, the same tag could be detected anywhere within a range of 120 to 150. As a result, non-normalized levels would be error prone.

To correct for the gain drift, a normalization procedure similar to that described above in reference to FIGS. 6A-6B may be performed. However, unlike the case in FIGS. 6A-6B, the open channel voltage in the bright mode is not constant over time, so the single value normalization described above (i.e., divide everything by $P_0$) fails to normalize the entire signal over time. Instead of the constant normalization, a more complex variable normalization can be applied, e.g., the normalization can be accomplished by dividing each raw bright-mode measured ADC value with an estimate of that point's open channel value. For each non-threaded region, an estimate of the open channel voltage can be made by any number of ways, e.g., by taking a local mean value or by using more sophisticated signal processing technique such as an integrated histogram technique, as described in more detail below. Thus, a local estimate can be obtained for the open channel value for the bright mode, so as to normalize a data point using the estimated voltage that is local to that data point.

On the other hand, the threaded regions of the signal can provide a challenge. For some threading events, there may open channel data available if the threading rate is slow enough, e.g., as shown in threading events 705 and 707. When the threading rate is relatively slow, open channel values can be measured before the tag is threaded. Such open channel values can be measured for each cycle. This behavior is depicted in the comb-like lines shown for threading event 705 and 707. In these cases, the limited open channel data may be used to estimate the true open channel value during the threading event. This limited open channel data (i.e., limited relative to when no threading occurs) can be used to obtain a local estimate of the open channel value (e.g., local within time, so as to account for gain drift)

However, it may be the case that the threading is fast enough that no open channel data is captured in the bright mode, e.g., as shown for threading events 709 and 711. When the threading rate is sufficiently fast, the tag is immediately threaded, and no open channel values are measured. This lack of open channel voltages can be problematic when trying to determine a local estimate of the open channel; if there are not open channel values for a given time interval, no local estimate can be determined for that time interval. In these cases, it is possible to determine the local estimate for the open channel data in the bright mode using the dark mode data, as described in further detail below.

C. Baseline Shift

Baseline shift is a phenomenon that is related to charge imbalances that build up on certain elements (e.g., $C_{Double\ Layer}$) in the cell during the charging and discharging cycles that take place during the measurement process. For example, during the measurement process, excess charge can build up on the working electrode of the cell, represented by $C_{Double\ Layer}$ in FIG. 4. In one example, the charge imbalance is caused by the fact that both the nanopore and the tags have non-linear I-V characteristics. As a result of this nonlinearity, a charge and discharge cycle may not add or remove the same amount of charge to the capacitive elements. For example, negative and positive ions may not move from one electrode to the other electrode via the pore at the same rate over time, e.g., causing positive charge to build-up in the well. Note that the duty cycle can be 60% dark mode and 40% bright mode to address a typical difference in transmission rate of positive and negative ions, but when a rate changes, the duty cycle would have to change, which can be difficult to do.

As a result of this accumulated charge imbalance, the voltage measurements in a cell would increase (e.g., when positive charge builds up in the well). This shift in a baseline voltage can increase until it produces a voltage high enough to counterbalance the opposing voltage originally set up as a consequence of the charge imbalance. At which point, the charge can re-balance. Baseline shifts can occur in the both the dark mode and bright mode open channel states and in each of the four threaded states, with the magnitude and time constants for the shifts potentially being different in each of the open channel and four threaded states. As a result, the baseline shift can change in a generally random way that mirrors the stochastic binding events of the tags at the pore.

Figure 8:
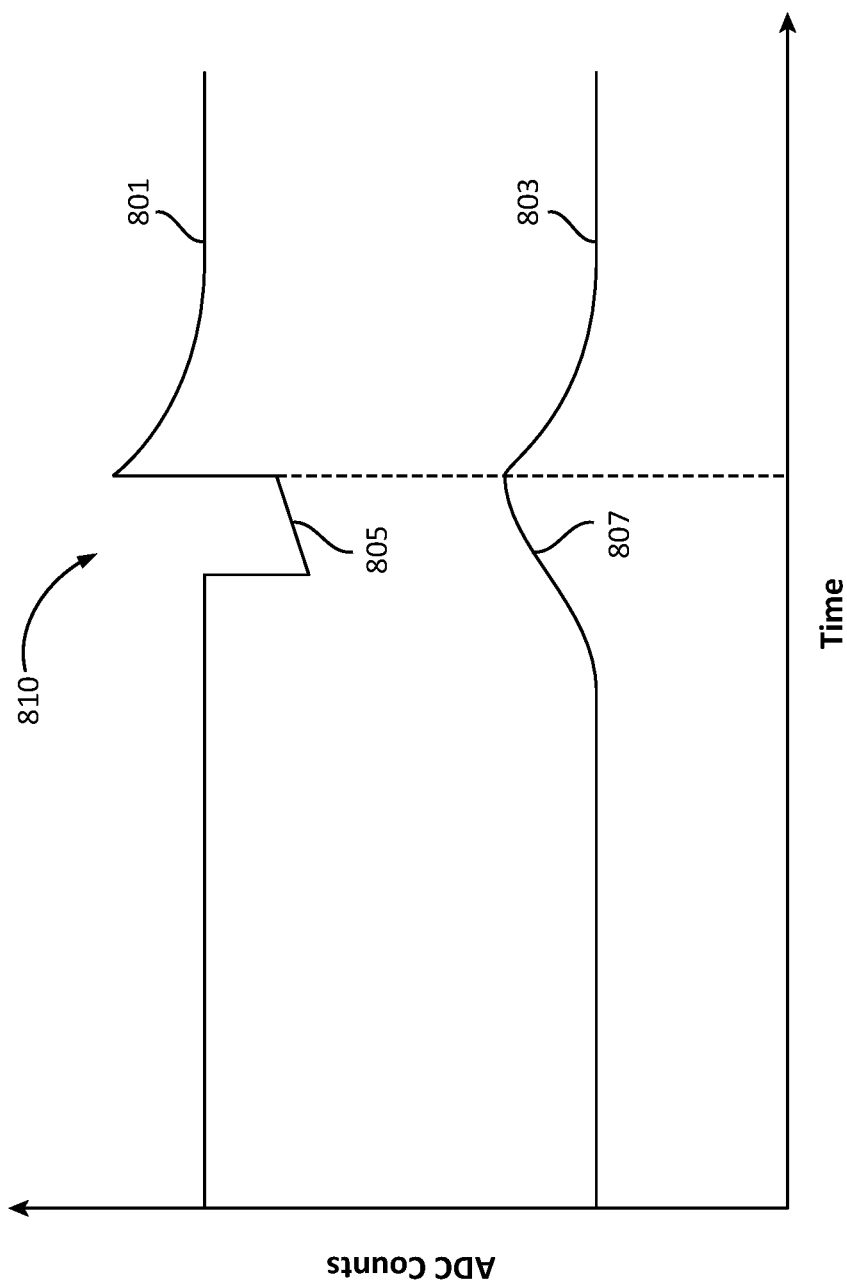
FIG. 8 shows an idealized signal that exhibits baseline shift according to certain embodiments.

FIG. 8 shows an idealized signal that exhibits baseline shift. Like FIGS. 6A-6B and FIG. 7, FIG. 8 shows an idealized bright mode data 801 and idealized dark mode data 803. This type of baseline shift generally occurs on a timescale that is on the order of the dwell time for a tag in a pore, a timescale that is generally much faster than the timescale for gain shift. Thus, gain shift is not shown in FIG. 8.

Before a threading event 810, the cell has reached equilibrium, i.e., the baseline voltage is what it needs to be to ensure equal charge transfer, e.g., to $C_{Double\ Layer}$ during the bright and dark modes. However, once the threading event 810 begins, the system is driven out of equilibrium. More specifically, while the effective resistance of the pore when the cell is in the dark mode stays the same, the effective resistance of the pore in the bright mode has increased. The increased resistance in the bright mode causes less charge to move during this mode, as compared to before the threading event occurred. Thus, a charge imbalance begins to form, which leads to upward shifts 805 and 807 in both the tag level and the dark mode open channel level, respectively.

As with the gain shift phenomenon, to compensate for baseline shift, a variable, point-by-point normalization can be applied, e.g., the normalization can be accomplished by dividing each raw bright-mode measured ADC value with an estimate of that point's open channel value. However, such a correction method can fail to properly normalize the threaded signals because of dynamical differences between the open channel and threaded channel signals. For example, if the open channel signal at time t is given by $P_{OC}(t)$ and the various threaded tag levels at time t are given by $P_i(t)$, where i=A, C, G, or T, the dynamics of the system can be modeled by the following two equations:

$$P_{OC}(t) = P_{OC}^0\left(1 + b*\left(1 - e^{-\frac{t}{T}}\right)\right) \quad (1)$$

$$P_i(t) = P_i^0\left(1 + b_i*\left(1 - e^{-\frac{t}{T}}\right)\right) \quad (2)$$

where $P_{OC}^0$ and $P_i^0$ are the values of the open channel and $i^{th}$ threaded channel at t=0, b is the open channel baseline shift at t=0, $b_i$ is the baselines shift at t=0 for the $i^{th}$ threaded channel, and T is the timescale associated with the baseline shift. A normalization method that relies on a point-by-point division of the bright mode data by a corresponding bright mode open channel signal can be effectively modeled by dividing equations (1) and (2) by equation (1), which yields Eqns. (3) and (4) for the normalized open-channel and tag levels, respectively:

$$P_{OC}^{NORM}(t) = 1 \quad (3)$$

$$P_i^{NORM}(t) = \left(\frac{P_i^0}{P_{OC}^0}\right)\frac{1 + b_i*\left(1 - e^{-\frac{t}{T}}\right)}{1 + b*\left(1 - e^{-\frac{t}{T}}\right)} \quad (4)$$

As can be seen in Eqns. (3)-(4) the OC levels are normalized perfectly for all time (by definition). In addition, if $b_i$=b then the time dependence drops out and Eqn. (4) reduces to $$P_i^{NORM}(t) = \left(\frac{P_i^0}{P_{OC}^0}\right) \quad (5)$$

However, in general, $b_i \neq b$ and the time dependence in Eqn. (4) remains resulting in the tag levels not staying constant for all time. Thus, any normalization of the tag levels that relies primarily on a point-by-point division by the open channel signal value can result in the normalized tag values still being time-dependent, even after normalization. The temporal variation of the tag levels, if large enough, can lead to downstream sequencing errors and it is therefore beneficial to employ signal processing techniques (in addition to point-by-point normalization by open channel values) to properly correct the data for baseline shift.

D. Variations in Zero Point Voltage

For electronic reasons, each cell can have a different zero-point voltage. The term zero-point voltage refers to the voltage output by a cell when 0 V is applied as input to the cell and is referred to herein as $V_0$. Variations in $V_0$ can be caused by manufacturing imperfections or variations between the analog circuitry of different cells in the chip. Also, for electrochemical reasons, a bias can be built into a cell. In addition, the surface chemistry of the electrodes may make them act as batteries, and thus each cell may have a slightly different potential that can contribute to the $V_0$ for each cell. The net effect of having a nonzero $V_0$ in a cell is that the measured ADC signal is artificially pushed up or down, depending on the value of $V_0$. Accordingly if $V_0$ varies over time, sequencing errors can result.

E. Sample Data Showing Gain Drift and Baseline Shift

Figure 9:
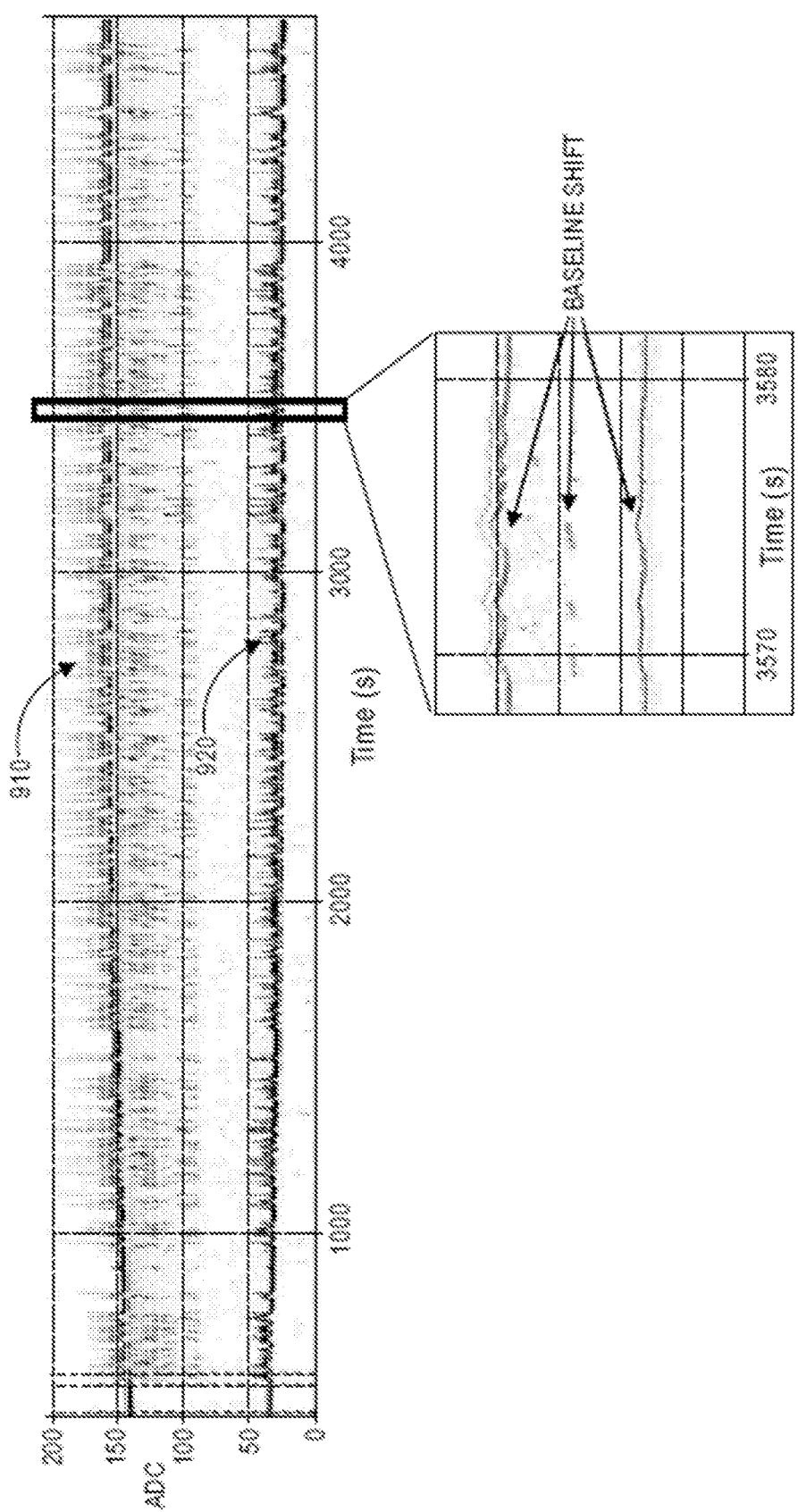
FIG. 9 shows one example of sample data for a raw sequencing signal that was measured from a nanopore cell over the course of approximately 5 seconds.

FIG. 9 shows one example of sample data for a raw sequencing signal that was measured from a nanopore cell over the course of approximately 5 seconds. The signal includes bright mode data 910 that includes multiple threading events and dark mode data 920. In response to threading events, both bright and dark mode data can suffer from relatively short term baseline shift as shown in the inset. On the longer time scale, e.g., on the order of seconds, the signal may also exhibit gain drift, which manifests in FIG. 9 as a slight and gradual change over time in the separation between the bright and dark channel signals. As can be seen in FIG. 9, the offset shift in the bright and dark channels is correlated, i.e., offset shift results in the bright and dark mode signals moving in the same directions, e.g., both modes shift upward or both shift downward. In contrast, gain drift is anti-correlated between the bright and dark channels, i.e., gain drift results in the bright and dark mode signals moving in opposite directions, e.g., if the bright mode drifts up the dark mode would drift down.

III. Signal Correction

A raw sequencing signal captured from a nanopore sequencing cell can suffer from a number of non-idealities including, e.g., gain drift, baseline shift, variations in the zero point voltage and other calibration issues as discussed above. One or more signal processing techniques can be employed to improve the raw sequencing signal such that sequencing errors are minimized.

The following sections describe methods for processing the raw sequencing signal to improve signal accuracy and stability. Section III(A) describes methods for correcting for and/or removing the effect of zero point voltage without explicit knowledge of any cell's $V_0$. Section III(B) describes methods that can minimize the effects of baseline shift, even when the dynamics of the open channel and threaded channel signals are different. Section III(C) describes methods that can be used to perform improved point-by-point normalization to correct for gain drift using open channel signal values that are tracked using a moving histogram technique. These methods may be used independently or in any combination to provide for improved signal processing methods in a nanopore sequencing cell.

A. Normalization without $V_0$

Embodiments can perform a calibration process to account for $V_0$ (also referred to as $V_{MZERO}$) as is described in U.S. patent application Ser. No. 15/632,190 entitled "Formation and Calibration of Nanopore Sequencing cells," the disclosure of which is incorporated by reference in its entirety for all purposes. For example, $V_0$ can be directly measured for each cell of the sequencing chip as part of a diagnostic routine that is run before each sequencing process. $V_0$ can be measured and updated regularly, stored in memory, and then subtracted from the measured bright mode and dark mode values before the performing 2D transformation processing and normalization procedures described above. However, inaccuracies can still result if the value of $V_0$ drifts from the stored value over the time period between the actual measurement of $V_0$ and the time that it is subtracted from the measured sequencing signal. According to certain embodiments, the system can employ improved processing methods that remove the requirement to track and remove $V_0$ and thus help alleviate errors caused by a time dependent $V_0$.

To illustrate an embodiment of the method it is useful to express the bright and dark mode voltage values in a functional from that expressly accounts for $V_0$ $$V_+ = m(V_{pos} - V_0) \quad (6)$$

$$V_- = m(V_{neg} - V_0) \quad (7)$$

where $V_+$ is the bright mode voltage measured by the ADC, $V_-$ is the dark mode voltage measured by the ADC, m is the gain of the system and $V_{pos}$ and $V_{neg}$ are voltages across the nanopore of the cell during the bright mode and dark mode respectively. Generally $V_{pos}$ can take 5 different values depending on the state of the nanopore: $V_{pos}^{OC}$ for the open channel state and $V_{pos}^{T_i}$ for each one of the threaded states corresponding to i=A, C, G, and T.

As described above in Section II(A), the normalization procedure can involve dividing the measured bright mode signal value by the corresponding open channel bright mode signal value. Using the functional form for the bright mode data introduced by Eqn. (6), the normalized values $f_i$ for each of the threaded states can be written in a form that explicitly accounts for the zero point voltage $V_0$ $$f_i = \frac{V_{pos}^{T_i} - V_0}{V_{pos}^{OC} - V_0} \quad (8)$$

where $V_{pos}^{T_i} - V_0$ is the measured bright mode threaded values for i=A, C, G, or T and $V_{pos}^{OC} - V_0$ is the measured bright mode open channel value.

Eqn. (8) shows that if $V_0$ changes over time, the particular numerical value for the normalized tag levels will also change, even if the raw threaded voltage $V_{pos}^{T_i}$ and the raw open channel voltage $V_{pos}^{OC}$ are each constant over time. Such a drift in the normalized tag levels can lead to downstream sequencing errors. As already briefly mentioned above, to correct for this source of error, the value of the zero point voltage $V_0$ can be measured frequently and subtracted from the measured open channel and threaded channel values before the normalization is done. However, this solution is problematic because it requires devoting valuable sequencing time to measuring $V_0$; and therefore introduces temporal blind spots or dead time into the sequencing process. According to certain embodiments, a modified normalization process can be employed that requires no prior knowledge of $V_0$ and thus does not require the measurement or tracking of $V_0$.

For example, an alternate normalization can be identified that does not depend on $V_0$ by recognizing that the zero point voltage $V_0$ shows up as merely an offset in both Eqs. (6) and (7). Accordingly, the offset can be eliminated by subtracting the dark mode data, expressed by Eqn. (7), from the bright mode data, expressed by Eqn. (6). Performing this subtraction on both the bright mode open channel data $V_+^{OC}$ and the bright mode threaded data $V_+^{T_i}$ results in the following alternative form for the normalization $$f_i' = \frac{V_{pos}^{T_i} - V_{neg}}{V_{pos}^{OC} - V_{neg}} = \frac{V_+^{T_i} - V_-}{V_+^{OC} - V_-} \quad (9)$$

This alternative form for the normalized values removes any explicit dependence on $V_0$ and thus $V_0$ need not be known to perform the normalization. Furthermore, the various terms in Eqn. (9) are each measured during a typical sequencing run and thus additional measurements are not required to perform the normalization. Additionally, if desired, the original normalized values, $f_i$, can be calculated from the redefined normalized values, $f_i'$ based on the following relationship $$f_i = f_i'(1 - f_-) + f_- \text{ with } i = A, C, G, \text{ or } T \text{ and } f_- = \frac{V_-}{V_+^{OC}}. \quad (10)$$

By subtracting the dark mode voltage from both the numerator and denominator of Eqn. (9) the effect of $V_0$ drift can be compensated for. In some embodiments, any variance in the raw signal values that is caused by a variance of $V_0$ is greatly reduced or even eliminated without needing to make any additional measurements to explicitly track $V_0$ during sequencing. As used herein the numerator and denominator of Eqn. (9) are referred to as the open channel and threaded channel zero point compensated signal values, respectively.

In view of the redefined normalization represented by Eqn. (9) it should be noted that the 2D transformation procedures described below in reference to Section III(B) can also benefit. More specifically, in the case of the rotation correction using the integrated history shown in FIGS. 12A-12C, the process can be modified by using the zero point compensated bright mode data as the input signal for the calculation of the integrated history (the x-axis). Likewise for the y-axis data, the zero point compensated bright mode data can be used. By using the compensated data any variance is caused by a changing $V_0$ in the bright mode data may be removed or minimized.

Figure 10:
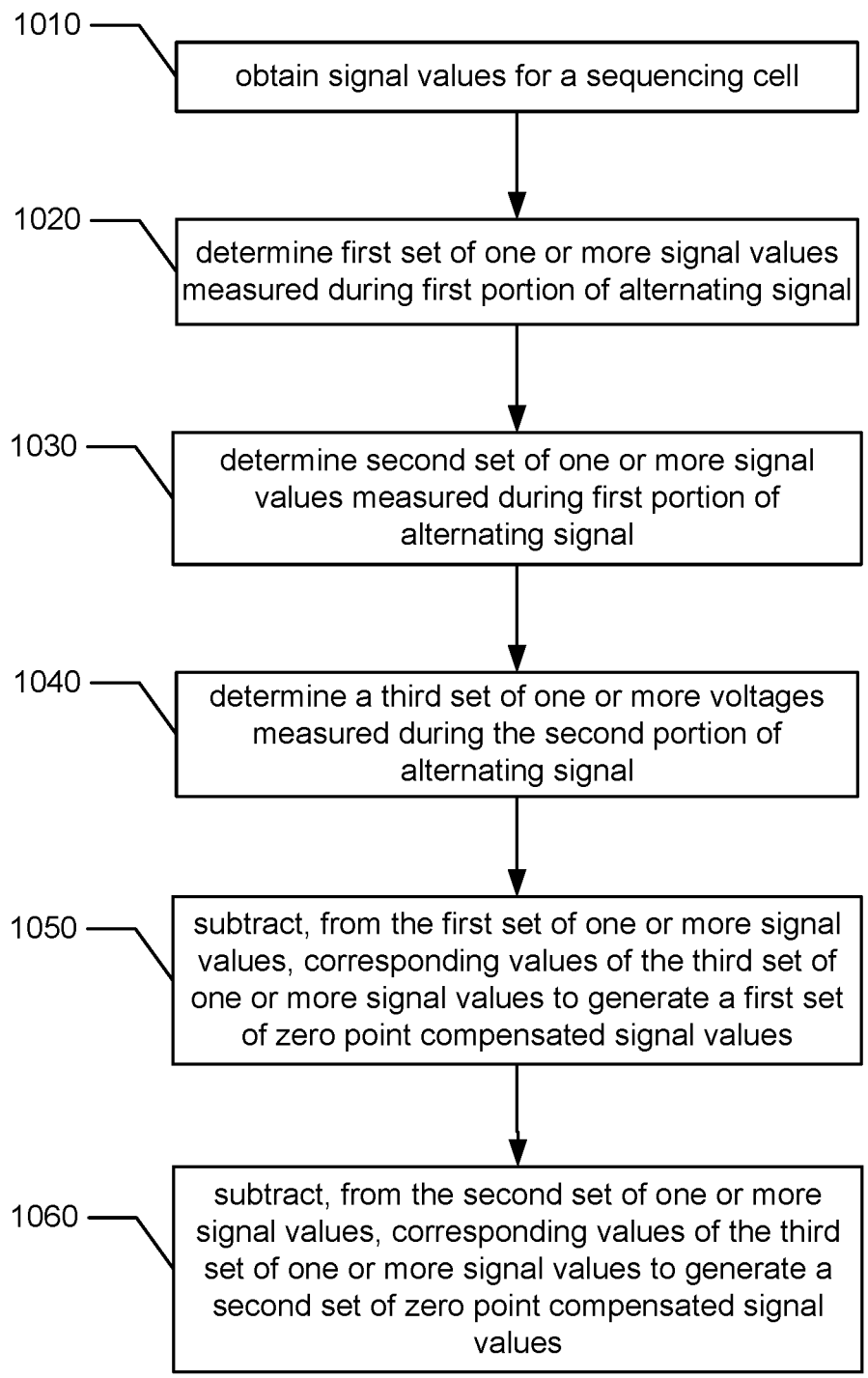
FIG. 10 shows a flow chart illustrating a method 1000 for processing a sequencing signal to remove the effects of a non-zero and varying $V_O$ according to certain embodiments.

FIG. 10 shows a flow chart illustrating a method 1000 for processing a sequencing signal to remove the effects of a non-zero and varying $V_0$ according to certain embodiments. In some embodiments, method 1000 may be performed by processor 224 of FIG. 2, digital processor 430, and/or any control logic coupled with the circuits of the sequencing cell.

In step 1010, multiple sequencing signal values $P(t_i)$ are obtained from the sequencing cell. The sequencing signal values can be voltages that are measured by an ADC and sent to a digital processor, e.g., ADC 410 and digital processor 430, as shown in FIG. 4. The digital processor can be part of a computer system that includes other components, e.g., as described in more detail below in reference to FIG. 20. The voltages may correspond to voltages that are measured over one or more bright periods that are themselves over one or more different AC cycles, i.e., it is not required that all the measured data be from the same bright period within a single AC cycle. Such measurements can occur as described herein and can occur at various times of sequencing different parts of a nucleic acid of a given cell. In some cases, the acquired voltages may vary from point to point (even for the same state of the nanopore) due to a variation in the zero point voltage of the cell over time. The applied voltage may be an alternating signal, e.g., an AC signal having a first portion (e.g., a bright period, also referred to herein as a "bright mode") and a second portion (e.g., a dark period, also referred to herein as a "dark mode") relative to a reference voltage. According to certain embodiments, the reference voltage may be a reference voltage (e.g., VPRE 405 in FIG. 4) that is applied to an integrating capacitor, e.g., ncap, as shown in FIG. 4.

In step 1020, a first set of one or more signal values is determined, e.g., one or more voltages measured during the bright period of the alternating signal are selected by the digital processor 430. The first set of voltages may correspond to various bright periods. Such measurements can occur as described herein and can occur at various times of sequencing different parts of a nucleic acid of a given cell. Furthermore, the first set of one or more signal values can correspond to various bright mode threaded channel signal values $V_+^{T_i}$ as described above in reference to Eqns. (6)-(9).

In step 1030, a second set of one or more signal values is determined, e.g., one or more voltages measured during the bright period of the alternating signal are selected by the digital processor 430. The first set of voltages may correspond to various bright periods. Such measurements can occur as described herein and can occur at various times of sequencing different parts of a nucleic acid of a given cell. Furthermore, the second set of one or more signal values can correspond to various bright mode open channel signal values $V_+^{OC}$ as described above in reference to Eqns. (6)-(9).

In step 1040, a third set of one or more signal values measured during the second portion of the alternating signal is determined, e.g., one or more voltages measured during the dark period of the alternating signal can be selected by the digital processor 430. The third set of one or more voltages can be measured across various dark periods and will correspond to the dark mode voltage signal values $V_-$ described above in reference to Eqns. (6)-(9).

In step 1050, corresponding values of the third set of one or more signal values are subtracted from the first set of one or more signal values, thereby generating a first set of one or more zero point compensated signal values. For example the subtraction shown in the numerator of Eqn. (9) can be performed by the digital processor 430. As described above, in reference to Eqn. (9), the resulting set of compensated bright mode threaded signal values will have a reduced variance due to the fact that the subtraction operation greatly reduces the effect of a fluctuating zero point voltage.

In step 1060, corresponding values of the third set of one or more signal values are subtracted from the second set of one or more signal values, thereby generating a second set of one or more zero point compensated signal values. For example the subtraction shown in the denominator of Eqn. (9) can be performed by the digital processor 430. As described above, in reference to Eqn. (9), the resulting set of compensated bright mode threaded signal values will have a reduced variance due to the fact that the subtraction operation greatly reduces the effect of a fluctuating zero point voltage.

Once the bright and dark mode zero point compensated signal values are determined, they may then be used in any other downstream signal processing method. For example, the open channel bright mode zero point compensated signal values may be used as normalization factors to normalize a set of bright mode threaded signal values. In some embodiments, the bright and/or dark mode compensated signal values can be further processed using a two-dimensional transformation to remove the effects of offset shift, as described below in Section III(B). In other embodiments, the bright mode compensated signal values may be used to form a histogram and this histogram can be used to obtain an improved estimate of the bright mode open channel value to be used for the normalization factor, as described below in Section III(C). Likewise, the zero point compensated signal values as determined by the above method can be determined by and output from the Zero Point Correction Module 1903, as described in further detail below in reference to FIG. 19.

B. Baseline Shift Removal by Two-Dimensional Transformation

As described above in reference to Eqns. (1)-(5), a point-by-point normalization technique can effectively correct for both gain drift and offset shift if the dynamics of the open channel signal and the threaded signals are the same. However, the dynamics of the open channel and threaded channel signals may not be the same. To better correct for both gain drift and baseline shift in the threaded signal, a method can be employed that processes a measured two-dimensional sequencing signal by way of a two-dimensional transformation, e.g., by using a rotation or a flattening transformation, as described in further detail below.

Figure 11:
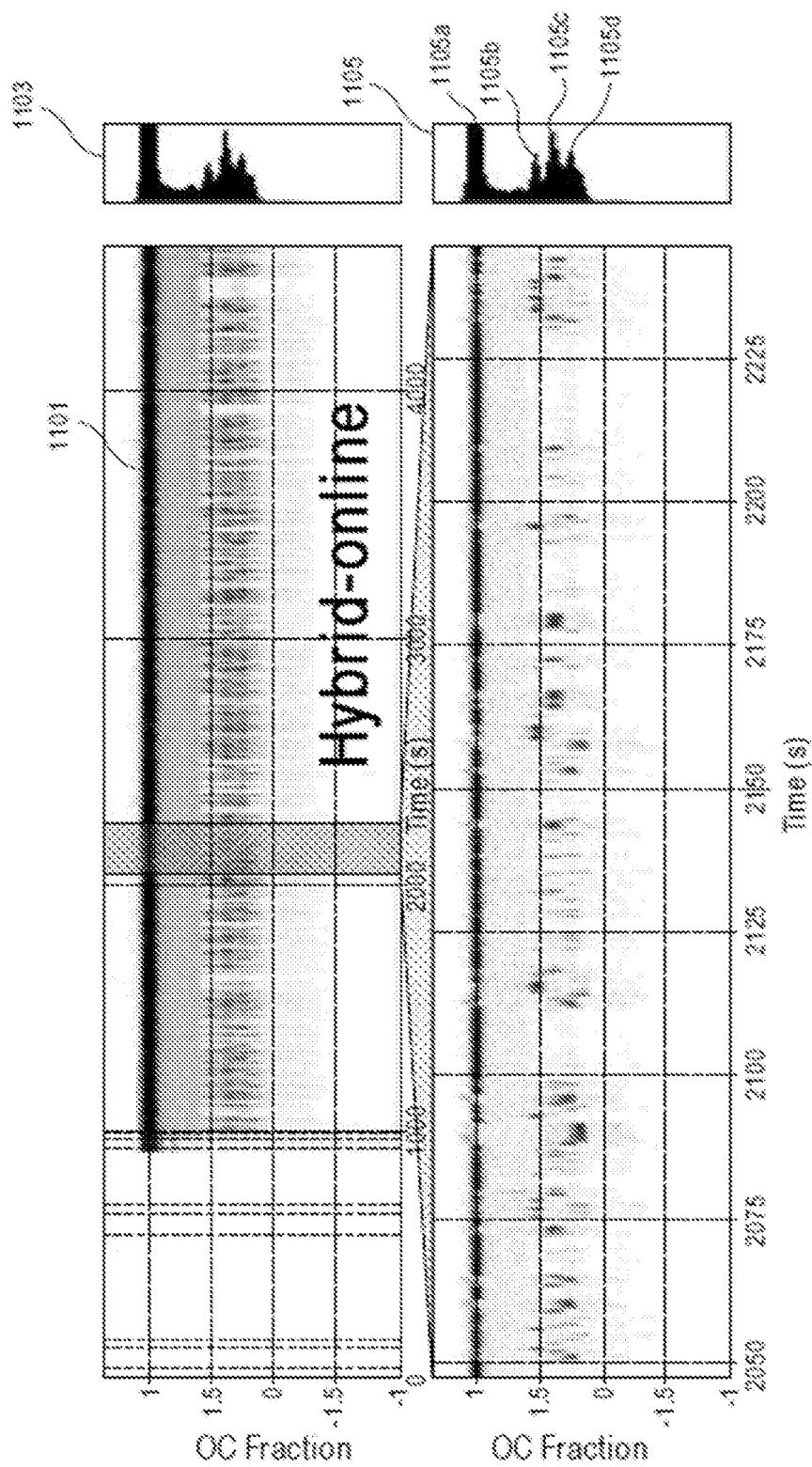
FIG. 11 shows an example of data that has been normalized using only a point-by-point open channel normalization routine that normalizes the measured bright mode signal using the open channel value according to certain embodiments.

The measured bright mode data can be represented by a one-dimensional array of signal values P ($t_i$) where, e.g., each point in the array is the bright mode signal value acquired at a time $t_i$. An example of such one-dimensional data is shown in FIG. 9, which shows bright mode data acquired over a time period of approximately 3.5 seconds. Ideally the values of the one-dimensional array P($t_i$) would only depend on the state of the nanopore and therefore would be consistent over time. In any real signal however, a given signal value that corresponds to a given pore state can vary in time and thus, the populations of signal values that correspond to the different nanopore states (open channel, and the four threaded states) are most accurately described by finite width distributions, each having some mean value. Stated another way, a histogram of the signal values acquired over some period of time will have 5 peaks of finite width, where the width of each histogram peak depends on the variance in the signal values that correspond to the different nanopore states. Histograms 1103 and 1105 in FIG. 11 show such examples. More specifically, histogram 1105 shows open channel peak 1105a and the threaded channel peaks 1105b, 1105c, and 1105d.

Having a large variance in a threaded channel value for a given pore state (e.g., a pore state corresponding to the threaded state of an "A" tag) is not ideal because it complicates the identification of that threaded tag (again, ideally a single threaded state would have a single consistent signal value over time). If the variance in one or more threaded state signal values are large enough, the signal value distributions for two different threaded states can overlap, making their identification within the sequencing signal difficult and error prone.

According to certain embodiments, the variance in the 1-dimensional data $P(t_i)$ can be accounted for and minimized by recognizing that the variance the 1-dimensional data $P(t_i)$ may be caused by the variation of some other uncontrolled variable that drifts or varies during the data acquisition period. For example, the particular value of $P(t_i)$ may depend on the amount of charge imbalance within the cell also at some time $t_i$, referred to herein as $Q(t_i)$. One way to account for the variance of $P(t_i)$ is to also measure the charge imbalance $Q(t_i)$ at every time $t_i$ and then process this two-dimensional data using some type of two-dimensional transformation to remove the variance in $P(t_i)$. More generally, each measurement of $P(t_i)$ can be paired with a measurement of another quantity $X(t_i)$, referred to herein as a correlated signal value to generate two-dimensional signal data point $S_{2D}=[X(t_i), P(t_i)]$. While the description below focuses on an example of two-dimensional signal data, the formalism can be extended to more than two dimensions without departing from the scope of the present disclosure.

This new two-dimensional dataset $S_{2D}$ can be used to find one or more two-dimensional transformations $R_{2D}$ that minimize the variance in the $P(t_i)$ dimension. In general, the two-dimensional transformation $R_{2D}$ can be represented as a two-by-two matrix as follows:

$$R_{2D} = \begin{bmatrix} \alpha & \beta \\ \gamma & \delta \end{bmatrix} \tag{11}$$

$S_{2D}$ can be represented as a column vector and thus the transformed signal values $S'_{2D}$ can be written as $$S'_{2D} = R_{2D} S_{2D} \tag{12}$$

$$\begin{bmatrix} X'(t_i) \\ P'(t_i) \end{bmatrix} = \begin{bmatrix} \alpha & \beta \\ \gamma & \delta \end{bmatrix} \begin{bmatrix} X(t_i) \\ P(t_i) \end{bmatrix} \tag{13}$$

$$X'(t_i) = \alpha X(t_i) + \beta P(t_i) \tag{14}$$

$$P'(t_i) = \gamma X(t_i) + \delta P(t_i) \tag{15}$$

According to certain embodiments, the correlated signal value $X(t_i)$ can be chosen to be anything that directly measures or is a proxy for a phenomenon that contributes to the variance of the bright mode signal values $P(t_i)$. For example, as described above, an offset shift may be the source of the variance in the measured $P(t_i)$ values because each measured bright mode point might have a slightly different offset shift. Furthermore, offset shift can be caused by a charge imbalance on one or more capacitive elements of the cell. Thus, to remove the variance in this example, the correlated signal value $X(t_i)$ should be chosen to be a measurement of the charge imbalance itself or a proxy for the charge imbalance, i.e., $X(t_i)$ should vary linearly with the charge imbalance. In the two examples that follow, the correlated signal value $X(t_i)$ is chosen to be either 1) a corresponding the dark mode signal value or 2) is what is referred to herein as an integrated history of the bright mode signal values. Both of these examples of the correlated signal value are proxies for, e.g., are linearly correlated with, the charge imbalance and can therefore be used to correct for offset drift in the bright mode signal data. As would be appreciated by one of ordinary skill in the art with the benefit of this disclosure, many other choices are possible for the correlated signal value.

In some embodiments, it can be beneficial to employ a 2D transformation that does not preserve the aspect ratio of the one or more clusters of data after they are transformed. For example such a 2D transformation is given by the transformation matrix $$R_{2D} = \begin{bmatrix} 1 & 0 \\ \rho_i & 1 \end{bmatrix} \tag{16}$$

Such a transformation can be beneficial because due to the fact that that in includes only a single transformation parameter $\rho_i$, also referred to herein as the "transformation parameter," it is computationally less demanding to both determine and apply to the data. In some embodiments, the transformation shown in Eqn (16) can be independently applied to different clusters of signal values in the 2D plane, possibly with different $\rho_i$'s being applied to different clusters, as described in more detail below. For example, a transformation parameter that is to be applied only to a cluster of bright mode open channel data (e.g., cluster 1201 in FIG. 12A) is referred to as $\rho_{OC}$, and a transformation parameter that is to be applied only to the group of bright mode threaded channel data clusters (e.g., clusters 1203, 1205, 1207, and 1209) is referred to as $\rho_{Th}$. In each case, the reduced transformation results in a linear mixing between the two dimensions of the signal data. For example, for the case of transforming bright mode open channel data $P_{OC}(t_i)$, the transformed open channel data $P'_{OC}(t_i)$ is given by the following equation $$P'_{OC}(t_i) = P_{OC}(t_i) + \rho_{OC} X(t_i) \tag{17}$$

And thus, the transformed signal value is the raw open channel signal value with some contribution from the correlated signal value added to it. The contribution from the correlated signal value is determined by the magnitude of the transformation parameter $\rho_{OC}$.

In accordance with some embodiments, the transformation parameter $\rho_{OC}$ is determined to be the transformation parameter that results in the flattest cluster of transformed open-channel data $P'_{OC}(t_i)$, e.g., the slope of a line fit through the transformed cluster is zero.

Threaded signal values can also be transformed similarly. For example the following transformation can be applied $$P'_{Th}(t_i) = P_{Th}(t_i) + \rho_{Tr} X(t_i). \tag{18}$$

The transformation parameter $\rho_{Th}$ can be chosen to provide for maximal distinguishability between then threaded peaks within a histogram of the data as described more detail below.

In illustrative examples disclosed herein, the particular form for the 2D transformation can be determined by finding the 2D transformation that maximizes the distinguishability between the different peaks in a histogram of the measured data. The histograms can be calculated from the measured time series data of the signal values by counting the number of signal values that fall within certain bins, where the bins span the dynamic range of the signal values (measured as either voltage or ADC counts). FIG. 11 shows histogram 1103 that is calculated using raw data and, as a result, has poor distinguishably between peaks, e.g., peak 1105*d* is visible as one smeared peak when ideally it should be two separate peaks. In contrast, FIG. 16B shows histogram 1605 that is calculated using data that was previously transformed using a 2D transformation with peaks that are more distinguishable than the peaks of histogram 1103.

In some embodiments, the optimal 2D transformation can be computed by optimizing properties of the histogram and stored in memory to be used for subsequent sequencing runs and/or can be updated periodically. For example, the optimal 2D transformation can be determined to be the 2D transformation that minimizes the minimum values between peaks (or subset of peaks) in the histogrammed data. In another example, the optimal 2D transformation can be determined to be the 2D transformation that maximizes the distance between the peaks (or subset of peaks) of the histogram. In some embodiments, the histogram can be modeled using a mixture model, e.g., a Gaussian or Laplacian mixture model, and the various parameters of the model, e.g., peak locations, minima values, etc.) can be used as parameters in an optimization function for determining the best 2D transformation.

In some embodiments, the optimal 2D transformation can be the transformation that leads to the flattest set of clusters or subset of clusters in the 2D plane. Such a transformation can be found by determining the 2D transformation that minimizes cluster mixing when the clusters of the 2D data are partitioned using horizontal lines (i.e., using thresholds that are constant in the x-dimension).

For the sake of simplicity, the illustrative examples discussed herein assume that the signal acquisition time is the same for both the bright mode signal values and the correlated signal values. However this need not be true in other embodiments and the bright mode and correlated signal values may be acquired at different times as long as some association can be made between the bright mode value measured at one time and the correlated signal value made at some other time.

I. 2D Transformation in the Dark-Bright Plane

According to certain embodiments, the dark mode signal data is chosen to be the correlated signal value $X(t_i)$ that has a corresponding value for each measured bright mode signal value $P(t_i)$. In this example, the dark mode signal is also used as a proxy for the charge imbalance induced baseline shift in the raw sequencing signal. Accordingly, a dark mode signal value can be measured and paired with each bright channel signal value to generate a two-dimensional sequencing signal $S_{2D}$ that can then be used to find a two-dimensional transformations $R_{2D}$ that minimize the variance in the bright mode signal $P(t_i)$.

Returning briefly to FIG. 9, it can be seen from the inset that both bright and dark channel data suffer from the baseline shift phenomena. Furthermore, it can be seen that the baseline shifts for bright mode data 910 and dark mode data 920 are correlated. According to certain embodiments, an improved method for correcting for offset shift in the bright mode data can leverage this correlation. For example, a two-dimensional sequencing signal $S_{2D}=[X(t_i), P(t_i)]$ can be captured, where in this case the correlated signal values $X(t_i)$ corresponds to the acquired dark mode signal values. This two-dimensional sequencing signal can then be used to identify a two-dimensional transformation $R_{2D}$ that when applied to the two-dimensional sequencing signal, reduces the variance in the bright mode signal data $P(t_i)$. For the sake of simplicity, this transformation will be referred to herein as a "rotation" in the dark-bright plane, but generally any two-dimensional transformation (not just rotations) may be employed without departing from the scope of the present disclosure. Furthermore, as would be appreciated by one of ordinary skill in the art with the benefit of this disclosure, a rotation of the data clusters or a rotation of the coordinate system are equivalent and thus, either method can be employed without departing from the scope of the present disclosure.

Figure 12A:
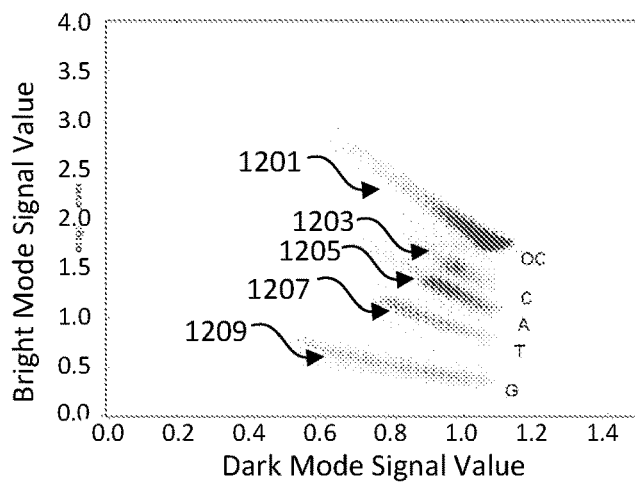
FIGS. 12A-12C show offset shift correction by rotation in the dark-bright plane according to certain embodiments.
Figure 12B:
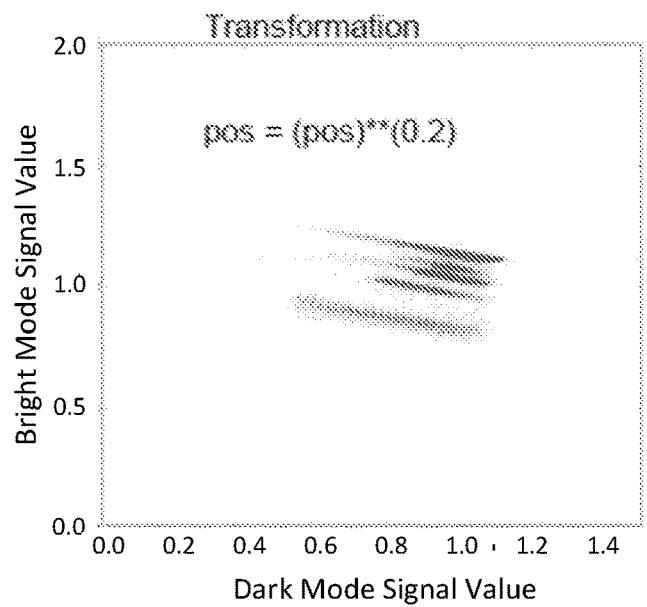
Figure 12C:
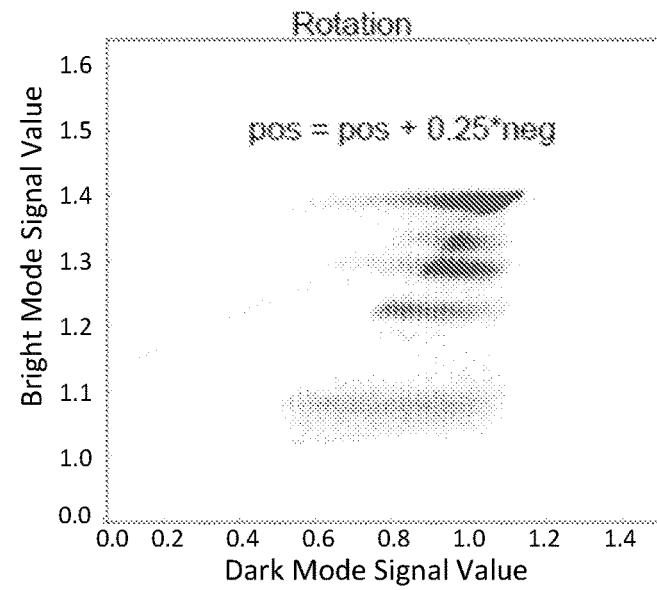

FIGS. 12A-12C show offset shift correction by rotation in the dark-bright plane according to certain embodiments. FIG. 12A shows an example of a plot of a two-dimensional sequencing signal $S_{2D}=[X(t_i), P(t_i)]$ in the dark-bright plane in order to illustrate the starting point for the method. More specifically, the x-coordinate of any point is given by a dark mode value $X(t_i)$ measured at time $t_i$ and the y-coordinate is the corresponding bright mode value $P(t_i)$. According to certain embodiments, the respective measurement times for the bright and dark points that comprise $S_{2D}$ need not be the same or simultaneous, but instead may be different times without departing from the scope of the present disclosure. In some embodiments, a bright mode signal value is paired with a dark mode signal value based on time, e.g., the first acquired bright mode point in a bright mode period is paired with the first acquired dark mode point found in the next dark mode period, or, e.g., the bright mode signal value is paired with a dark mode value that is either immediately before or immediately after the bright period from which the bright mode signal value is acquired, such that the duration of time between the bright and dark mode signal values is as small as possible. In other examples, an average dark mode value is paired with one or more bright mode values. Many other combinations are possible as can be appreciated by one of ordinary skill in the art having the benefit of his disclosure.

As can be seen in FIG. 12A, plotting the data in the dark-bright plane shows that the various data points $S_{2D}$ form natural clusters 1201, 1203, 1205, 1207, and 1209, representing the open channel measurements and threaded values for the four different tags corresponding to the C, A, T, and G bases, respectively. These clusters are generally elongated in shape, with their major axes pointing up and to the left, i.e., not horizontal relative to the dark mode axis. Thus, the preprocessed data is not optimized to minimize the variance of the data in the $P(t_i)$ dimension (i.e., the vertical dimension). In fact, the natural shape of the data clusters hints at the fact that a two-dimensional transformation $R_{2D}$ exists that can rotate and/or flatten each individual cluster such that the variance in the $P(t_i)$ dimension is minimized.

Before the data is transformed in the dark-bright plane, the data may be preprocessed by scaling to either compress or extend the dynamic range of the signal in one or more directions. For example, FIG. 12B shows the original signal, with the y-axis values scaled by taking these values to the ⅕ power, i.e., $y_{transformed}=y^{1/5}$. In this example, the original y-range of the data spanned (approximately) from 0.5 to 2.5 and after the scaling transformation the y-range is compressed to span (approximately) from 0.7 to 1.4. As would be appreciated by one of ordinary skill in the art with the benefit of this disclosure, this scaling step is optional and, in addition, any form of scaling function (in either the x or y dimension) may be applied without departing from the scope of the present disclosure.

FIG. 12C shows the resulting data after $R_{2D}$ is applied to the two-dimensional data. In this example, the 2D transformation $R_{2D}$ leaves the x-coordinate of each raw data point unchanged and maps the y-coordinate to a new position:

$$x_t^{R2D}=x_t \tag{19}$$

$$y_t^{R2D}=y_t+0.25x_t \tag{20}$$

Alternatively the 2D transformation can be represented by the matrix multiplication $$R_{2D} = \begin{pmatrix} 1 & 0 \\ 0.25 & 1 \end{pmatrix} \begin{pmatrix} x \\ y \end{pmatrix} \quad (21)$$

where in this case, the x-component is given by the dark mode value and the y-component is given by the bright mode value as already described above in reference to FIGS. 12A-12C.

In the example described above, the same transformation $R_{2D}$ is applied to every data point regardless of which cluster it belongs to. According to certain embodiments, independent transformations can be applied to each data point, based on the cluster that the data point belongs to. For example, the open channel data cluster can be flattened/rotated using one transformation, the threaded C cluster can be flattened/rotated by a different transformation. In some embodiments, the open channel cluster can be transformed using one transformation while the four clusters representing the threaded values can be transformed using a different transformation. Likewise, for applications that use dark mode data, the dark mode data cluster can be transformed using a third transformation that is different from the transformation used on the bright mode open channel and threaded values. In general, the precise entries for the 2D transformation $R_{2D}$ may be determined numerically by, e.g., optimizing the transformation such that a linear fit to the transformed data has zero slope, or e.g., by finding the transformation that maximizes the separation between the threaded levels.

2. 2D Transformation in the Integrated History—Bright Mode Plane

Rather than using the dark mode signal values, as described above, according to certain embodiments, a form of running average of the bright mode data, what is referred to herein as the "integrated history" of the bright mode data, is chosen to be the correlated signal value $X(t_i)$. In this example, the integrated history signal is also used as a proxy for the charge imbalance induced baseline shift in the raw sequencing signal. Accordingly, an integrated history signal value can be measured and paired with each bright channel signal value to generate a two-dimensional sequencing signal $S_{2D}$ that can then be used to find a two-dimensional transformations $R_{2D}$ that minimize the variance in the bright mode signal $P(t_i)$.

The integrated history may be computed by summing (i.e., integrating) the historical bright mode data over a certain time window to compute a single integrated history value. In some implementations, the integrated history may be computed on a running basis for each newly acquired measured bright mode data point $P(t_i)$. This can be accomplished using a recurrence relation (like that shown in Eqn. (22) below) that computes a corresponding updated integrated history value $H(t_i)$ using the prior value of the integrated history $H(t_{i-1})$. Older data points may also be discounted over time, e.g., historical data may be effectively discounted exponentially as that value ages by scaling this data by a weighting factor that decreases as the age if the data increases, e.g., as is done in Eqn. (22) below.

In other implementations the age of each acquired data point to be used for the integration can be stored separately and then used to apply a data point specific weighting factor before the integration is computed. For example, an exponential weighting factor $$A = e^{-\frac{ndt}{T}}$$

can be applied to each acquired data points and the integration is then performed by summing up all of the individually the weighted points. In this example, dt is the acquisition period (measured in seconds), n is the age of the data point (the number of acquisition periods that have elapsed since the data point was acquired), and T is an exponential decay parameter that can be chosen based on how quickly one desires to downgrade the contribution of the historical data to the integral.

Returning to the example of an integrated history computed by recurrence relation, the time weighted integrated history process described above may be implemented by software, hardware or any combination thereof that results in a computation of the following recurrence relation:

$$H(t_i) = (1-\alpha)H(t_{i-1}) + \alpha P(t_i) \quad (22)$$

where $0 < \alpha < 1$ is a constant that parameterizes how much to weight the historical data relative to the current data point when computing each integrated history. The parameter $\alpha$ is referred to as the decay rate and is given by $$\alpha = 1 - e^{-\frac{dt}{aT}} \quad (23)$$

where dt is the acquisition time step and T the measured time constant associated with the step response of the working electrode in the cell, and $\alpha$ is a "memory rate" parameter that can be set to increase or decrease the time it takes the algorithm to "forget" the historical data, i.e., it can set how quickly the historical data is downgraded. Eqn. (22) has the beneficial property that the nominal value of $H(t_i)$ is equal to the nominal value of the input. For example, during long open channel periods, i.e., long periods with no threading events, the integrated history equals the open channel level.

To form the 2D data points, a bright mode data point that is measured at time $t_i$ is associated with a corresponding integrated history value $H(t_i)$, and these two points can form the two-dimensional sequencing signal $S_{2D} = [H(t_i), P(t_i)]$ to be processed as 2-dimensional data, similar to the process described above in reference to FIGS. 12A-12C. For example, the transformed data can be computed using the following equation $$P'_k(t_i) = \frac{P_k(t_i) + \rho_k H(t_i)}{1 + \rho_k} \quad (24)$$

where the index k runs over the different clusters that are being transformed, e.g., open channel or threaded channel clusters. For example, one transformation with the transformation parameter $\rho_{OC} = 0.01$ could be applied to flatten the open channel data cluster and a different transformation with the transformation parameter $\rho_{Th} = 0.02$ could be applied to flatten the threaded data clusters.

For example, for the case of the threaded values, the transformed signal values can be computed by the following equation $$P'_{Th}(t_i) = \frac{P_{Th}(t_i) + \rho_{Th}H(t_i)}{1 + \rho_{Th}} \quad (25)$$

The transformed threaded signal values $P'_{Th}(t_i)$ can then be normalized according to the following equation $$N_{Th}(t_i) = \left(\frac{P'_{Th}(t_i)}{P'_{OC(t_i)}} - 1\right)(1 + \rho_{th}) + 1 \quad (26)$$

where the mathematical operations in addition to the division of $P'_{Th}(t_i)$ by $P'_{OC}(t_i)$ are added to keep the normalized levels $N_{Th}(t_i)$ in the range from 0 to 1 and also to keep the threaded tag fractions constant for all values of $\rho_{th}$. Accordingly, if $\rho_{th}$ is small, Eqn (26) reduces to usual normalization defined above in Eqn (5), i.e., $$\frac{P'_{Th}(t_i)}{P'_{OC}(t_i)}.$$

In some embodiments, the dark mode data can also be transformed via two dimensional transformation to flatten this data to remove the effects of baseline shift. For example the raw dark mode data $D(t_i)$ can be transformed according to the following equation $$D'(t_i) = \frac{D(t_i) + \rho_D H(t_i)}{1 + \rho_D}, \quad (27)$$

where $D(t_i)$ is the dark mode signal value and $\rho_N$ is the transformation parameter determined to flatten/rotate the dark mode data cluster and $H(t_i)$ again is the integrated history of the bright mode signal. In some embodiments, the transformed dark mode data $D'(t_i)$ can be used for optional zero point correction as described above in reference to Section III(A). In that case, to minimize noise propagation from the negative channel to the positive channel, the flattened negative channel data can be filtered through an exponential filter before it is used. In some embodiments, the dark mode level can be tracked with a moving histogram like the bright mode open channel values, as described below in reference to Section III(C).

Figure 13A:
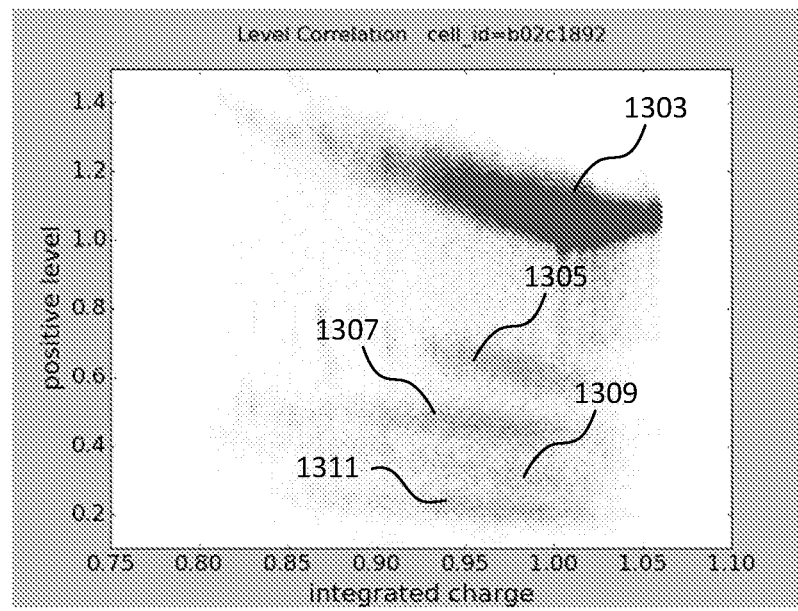
FIGS. 13A-13B show plots that illustrate a method for offset shift correction by transformation in the 2D plane defined by the integrated history value and bright value according to certain embodiments.
Figure 13B:
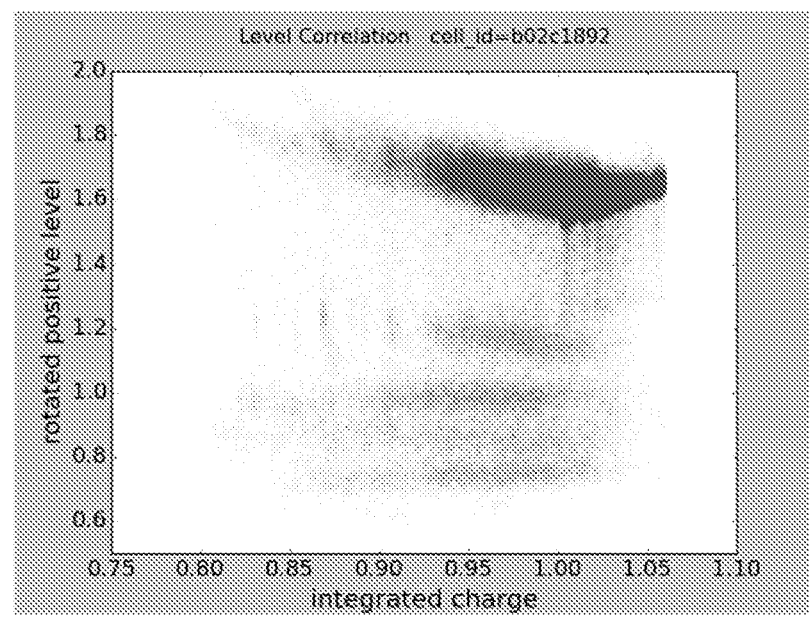

FIGS. 13A-13B show plots that illustrate a method for offset shift correction by transformation in the 2D plane defined by the integrated history value and bright value according to certain embodiments. Plotted in this two-dimensional space, the relevant bright mode signals, e.g., OC, A, C, G, and T, clearly show up as five distinct clusters of data points 1303, 1305, 1307, 1309, and 1311, respectively. Like the clusters described above in reference to FIGS. 12A-12C, they are tilted relative to the horizontal axis (the integrated history axis).

According to certain embodiments, the processing of the 2D data shown in FIGS. 13A-13B takes place in a manner that is similar to that described above in reference to FIGS. 12A-12C and the details will not be repeated here for the sake of conciseness. Like FIG. 12C, FIG. 13B shows "rotated" or "flattened" data having separations between the various levels that is improved relative to the unprocessed data.

3. Illustrative Flow Charts for 2D Transformation Methods

Figure 14:
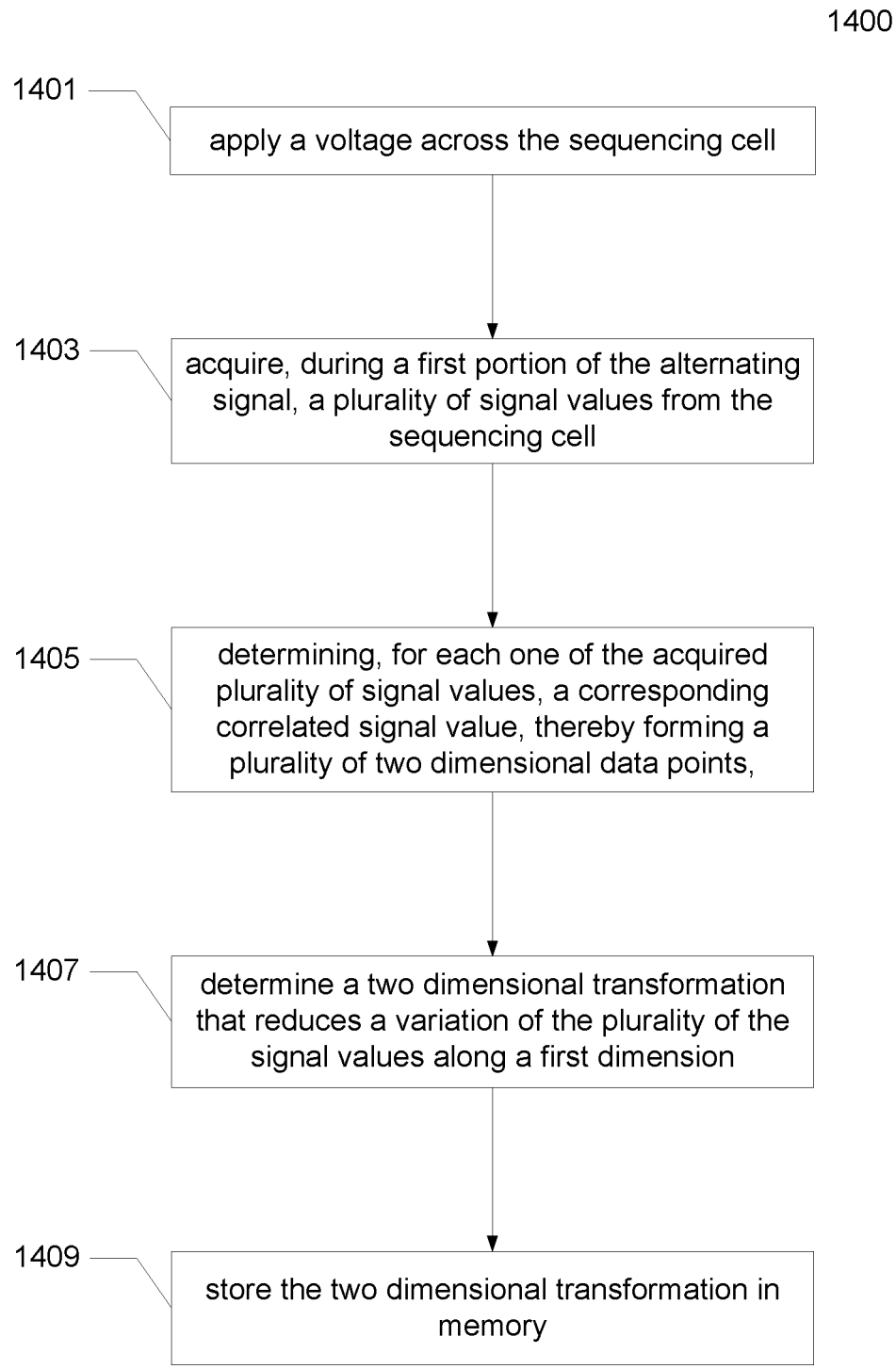
FIG. 14 shows a flow chart that illustrates a method 1400 of using a sequencing cell, according to certain embodiments.

FIG. 14 shows a flow chart that illustrates a method 1400 of using a sequencing cell, according to certain embodiments. More specifically FIG. 14 describes a method for determining a two-dimensional transformation that can be used to correct sequencing signal data. In some embodiments, method 1400 may be performed by processor 224 of FIG. 2, digital processor 430, and/or any control logic coupled with the circuits of the sequencing cell.

In step 1401, a voltage can be applied across a sequencing cell that includes a nucleic acid. The applied voltage may be an alternating signal, e.g., an AC signal having a first portion (e.g., a bright period, also referred to herein as a "bright mode") and a second portion (e.g., a dark period, also referred to herein as a "dark mode") relative to a reference voltage. According to certain embodiments, the reference voltage may be a reference voltage (e.g., $V_{PRE405}$ in FIG. 4) that is applied to an integrating capacitor, e.g., $n_{cap}$, as shown in FIG. 4.

In step 1403 multiple sequencing signal values $P(t_i)$ are acquired from the sequencing cell. According to some embodiments, the sequencing signal values can be voltages that are measured by an ADC and sent to a digital processor, e.g., ADC 410 and digital processor 430, as shown in FIG. 4. The digital processor can be part of a computer system that includes other components, e.g., as described in more detail below in reference to FIG. 20. The voltages may correspond to voltages that are measured over one or more bright periods that are themselves over one or more different AC cycles, i.e., it is not required that all the measured data be from the same bright period within a single AC cycle. Such measurements can occur as described herein and can occur at various times of sequencing different parts of a nucleic acid of a given cell. In some cases, the acquired voltages may vary from point to point (even for the same state of the nanopore) due to a variation in the offset shift of the cell. Accordingly, the set of acquired voltages taken as a population will have some variation (quantified as a variance) that is due at least in part to the variation in the offset shift.

In step 1404, a set of corresponding correlated signal values $X(t_i)$ are determined by, e.g., by the digital processor. As described above in Section III(B)(1)-(2), the correlated signal values can be determined a number of different ways, e.g., by taking a corresponding dark mode value or by computing a corresponding integrated history value (integrated histories). In either case, the data of the originally 1-dimensional measured signal values $P(t_i)$ is expanded into a set of two-dimensional data points $S_{2D}=[X(t_i), P(t_i)]$, where each signal values $P(t_i)$ measured at time $t_i$ is paired with a corresponding correlated signal value $X(t_i)$.

In step 1405, a two-dimensional transformation that reduces the variation of the plurality of measured signal values is determined by the digital processor. In some embodiments, the two-dimensional transformation is determined such that when it is applied to the set of two-dimensional data points, it compensates for the variance in the voltage offset shift of the cell. More specifically, for two-dimensional data that can be expressed in a two-dimensional space defined by the values $[X(t_i), P(t_i)]$ the transformation is chosen to minimize the variance (i.e. to flatten the data) in the $P(t_i)$ dimension, i.e., the dimension defined by the originally measured bright mode signal values $P(t_i)$. In some embodiments, the two-dimensional transformation can take the form of Eqns. (11) and/or (16) above.

As described above in reference to FIGS. 12-13, the data $S_{2D}$ can naturally form data clusters, e.g., five data clusters corresponding the open channel state of the nanopore and the four threaded states of the nanopore. In some embodiments, a single two-dimensional transformation is chosen that transforms all the of the clusters in the same way, e.g., rotates all clusters by some angle φ. In such a case, the transformation can be chosen to minimize the variance of one cluster only, to minimize the variance of more than one cluster simultaneously, or to maximize the separation between clusters, as described above in Section III(B). In other embodiments, more than one transformation can be employed, e.g., five different transformations can be found that transform the five data clusters differently to minimize the variance in each cluster separately.

In step 1407, the two-dimensional transformation is stored in memory, e.g., in a memory that is accessibly by the digital processor and/or a computer system that has been programed to transform the sequencing signal data as it is acquired.

Once a two-dimensional transformation is determined and stored in memory, it can be used to process sequencing signal data to reduce or minimize the effects of baseline shift on the signal values. For example, each new processed data point can be computed from the measured signal data using Eqns. (24), (25), or (26) depending on the cluster the data point belongs to.

Figure 15:
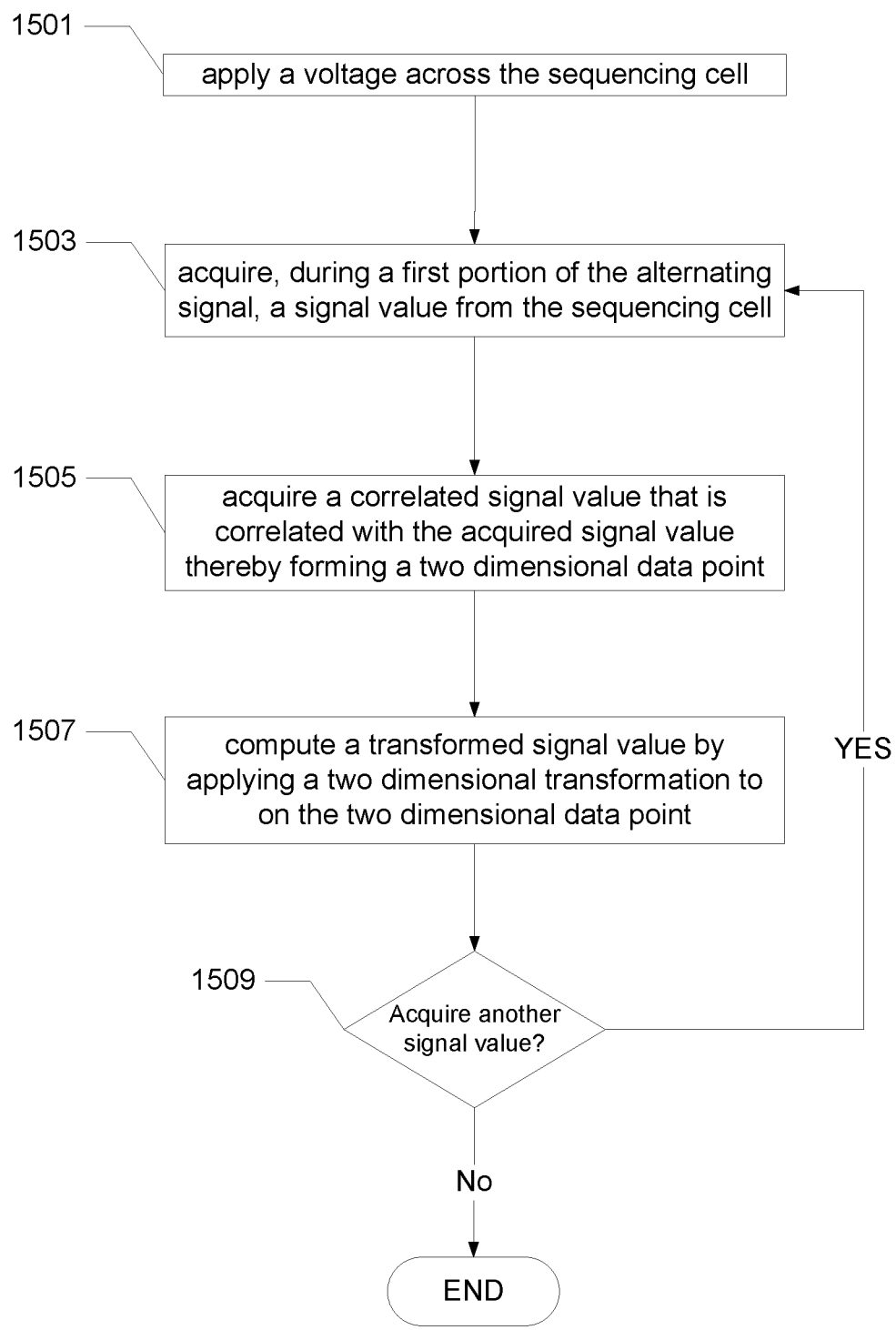
FIG. 15 shows a flow chart that illustrates a method of using a sequencing cell, according to certain embodiments.

FIG. 15 describes an acquisition and transformation loop that can provide for baseline shift removal by applying a two-dimensional transformation to sequencing signal data on a point-by-point basis, as new data points are acquired. In some embodiments, method 1500 may be performed by processor 224 of FIG. 2, digital processor 430, and/or any control logic coupled with the circuits of the sequencing cell.

In step 1501, a voltage is applied across the sequencing cell in a manner that is similar to that described above in reference to FIG. 14, step 1401.

In step 1503, one or more signal values from the sequencing cell are acquired during the first portion of the alternating signal. This step is again similar to that described above in reference to FIG. 14, step 1403.

In step 1505, one or more correlated signal values are acquired in a manner similar to that described above in reference to FIG. 14, step 1405.

In step 1507, one or more transformed signal values are computed by applying a two-dimensional transformation on the two-dimensional data points. For example, as described above in Section III, the two-dimensional transformation $R_{2D}$ can be applied to the two-dimensional data points $S_{2D}=[X(t_i), P(t_i)]$. According to certain embodiments, $R_{2D}$ can be represented as a 2-by-2 matrix and applying the transformation can involve performing a matrix multiplication $R_{2D}S_{2D}$. The components of $R_{2D}$ can be previously determined and accessible via memory, e.g., according to the method described above in reference to FIG. 14.

According to certain embodiments, the same transformation $R_{2D}$ can be applied to all the two-dimensional data points or different transformations can be applied to different classes or clusters of data points. For example, if the data point is determined to likely be an open channel data point (or belong to the cluster of open channel data points), an open channel specific transformation can be applied to that data point. Likewise, if a data point is determined to likely be a threaded data point (or belong to one or the four clusters of threaded tag data points), then a threaded-state specific transformation can be applied. Furthermore, it is also possible to apply tag specific transformations based on a determination that a data point is associated with the threaded state of a particular tag. According to certain embodiments, the particular category of the data point to be process can be estimated based on the raw value of the bright mode value of the data point, i.e., by the value of the raw $P(t_i)$ For example, one or more thresholds can be predetermined determined and the category of the data point can be estimated based on whether the value $P(t_i)$ is above, below, or within the threshold value(s). For example, $P(t_i)$ values above a certain threshold can be determined to be open channel values and thus an open channel specific transformation can be applied to these values. In some embodiment, each new processed data point can be computed from the measured signal data point by using Eqns. (24), (25), or (26) depending on the cluster the data point belongs to.

In step, 1509 a decision is made whether continue the acquisition and transformation loop, i.e., whether or not to acquire and process another data point. This consideration can take into account any number of factors, including, e.g., memory and/or bandwidth limitations or, e.g., whether or not the system was preprogramed to acquire and process a certain number of data points during the loop. While the example shown here illustrates a case where each data point is processed by two-dimensional transformation on a point-by-point basis, the transformation can be applied after acquiring a group of data points without departing form the scope of the present disclosure.

While the methods described above, e.g., in reference to FIGS. 14-15, relate to acquisition and transformation of signal values that represent voltages, other types of signals are possible and thus other types of signal values may be processed without departing from the scope of the present disclosure. For example, the circuitry of a cell may be configured such that signal values represent measurements of voltages, currents, or any other quantity (e.g., time) that may be used to derive the voltage and/or current at any point in a circuit of the sequencing cell.

4. Comparison of Point-By-Point Normalization to 2D Transformation

The raw bright mode data, e.g., raw sequencing signal 910 shown in FIG. 9, can be processed using a point-by-point open channel normalization routine that divides each measured bright mode data point by a corresponding measured (or estimated) bright mode open channel value. For example, such normalization methods may be used as described in U.S. patent application Ser. No. 15/632,190.

FIG. 11 shows an example of data that has been normalized using only a point-by-point open channel normalization routine that normalizes the measured bright mode signal using the open channel value (measured, if one is available, or estimated, if no measured value is available). The open channel values 1101 are normalized quite well; the data is generally flat and clustered around a value of 1. However, even in the normalized signal, the threaded values (tag levels) are poorly differentiated, as can be seen by the low contrast between threaded value peaks in the histograms 1103 and 1105.

Ideally, the histograms should have 5 sharply delineated peaks for the OC, A, C, G, and T threaded levels each separated by minima having approximately zero counts. Instead, the histograms show only four peaks that are easily distinguishable, e.g., peaks 1105a, 1105b, 1105c, and 1105d.

Furthermore, two of the threaded tag levels seem to be blurred together within the final peak 1105*d*. Such poor separation between the tag levels can lead to serious difficulty for any process tasked with identifying which base is being sequenced at which time.

To provide improved differentiation between the threaded signal levels, one or more embodiments can preprocess the sequencing signal using one of the 2D transformations described above in reference to Sections III(B)(1)-III(B)(3) before applying any point-by-point normalization routine.

Figure 16A:
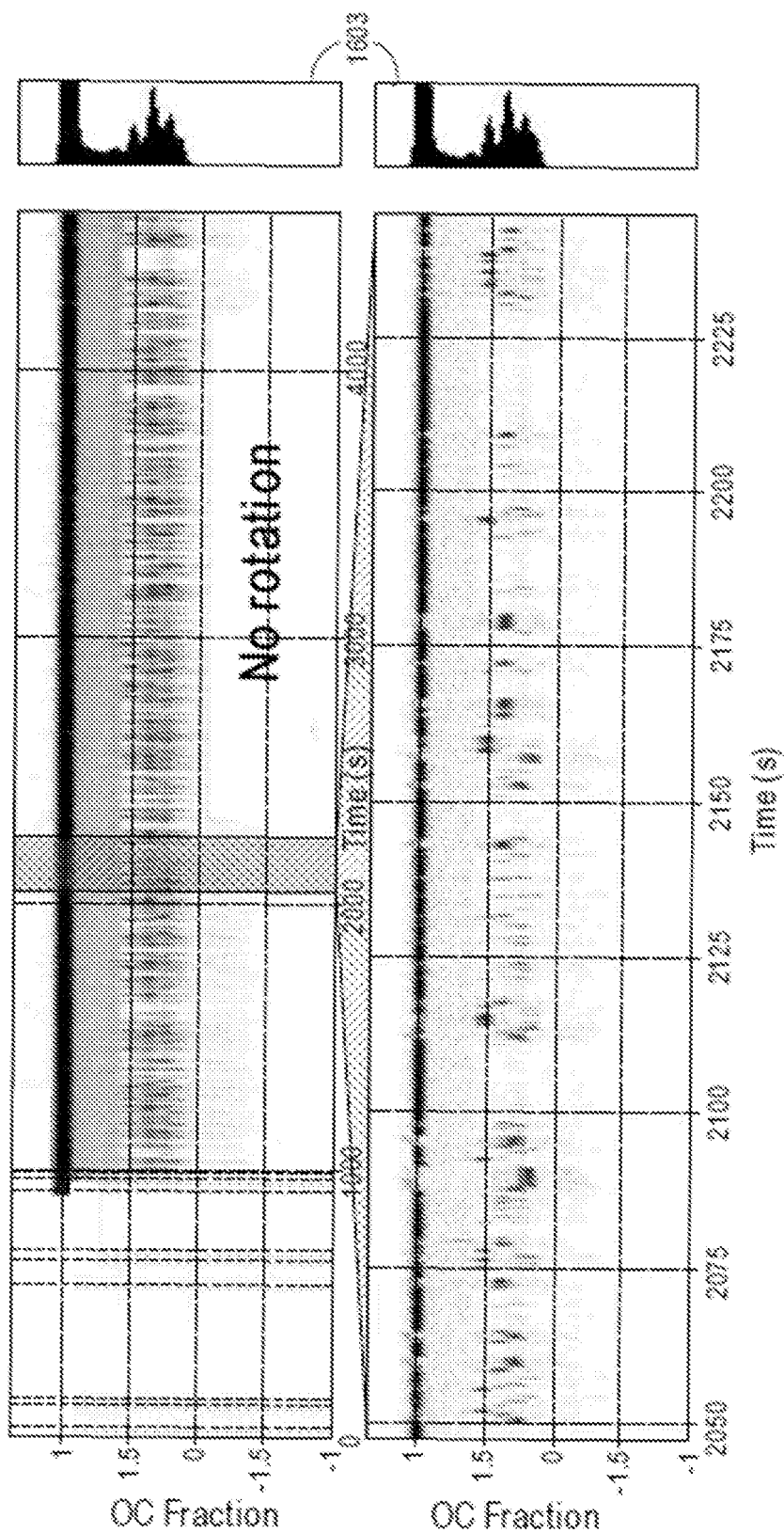
FIGS. 16A and 16B show a comparison of sample data processed by point-by-point normalization only and by two-dimensional transformation in the integrated history-bright mode plane followed by point-by-point normalization according to certain embodiments.
Figure 16B:
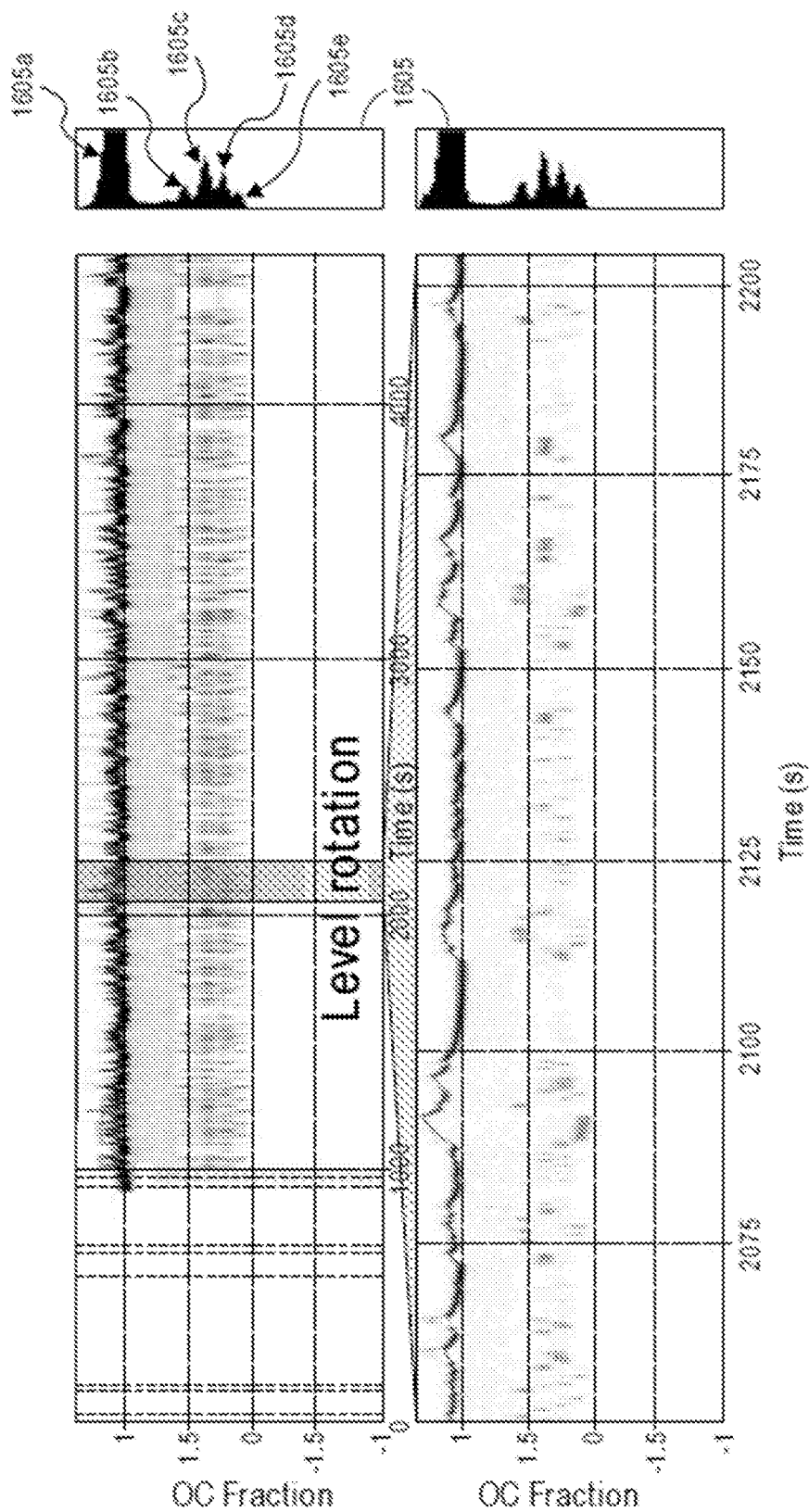

FIGS. 16A and 16B shows a comparison of sample data processed by point-by-point normalization only (FIG. 11 reproduced as FIG. 16A for convenience) and by two-dimensional transformation in the integrated history-bright mode pane followed by point-by-point normalization (bottom pane). As can be seen by the histograms 1603 and 1605 and the respective insets, the signal that has been preprocessed by 2D transformation using integrated history (shown in histograms 1605) has superior contrast to the bare point-by-point normalization (shown in histograms 1603) for all of the different signal levels. As compared to histograms 1603, histograms 1605 possess more distinguishable peaks for the open channel 1605*a* and the four threaded channels 1605*b*, 1605*c*, 1605*d*, 1605*e*. Accordingly, the processing technique that employs a two-dimensional transformation can provide for more accurate sequencing relative using only a point-by-point normalization technique.

C. Normalization Using Open Channel Tracking with Running Histogram

The bright mode open channel voltage can be tracked and used to normalize the raw sequencing signal, as briefly described above in Section III(A) and described in detail in U.S. patent application Ser. No. 15/632,190. One way to determine a bright mode open channel value to use for normalization is to choose a bright mode open channel data point that is closest in time to the data point that is to be normalized. In some situations, however, a suitable bright mode open channel value may not be present in the data. For example, for reasons having to do with threading dynamics, there may be very few, if any, open channel data points over the bright mode acquisition time period. Other methods can use a corresponding dark mode value to compute an estimated bright mode open channel value, but for certain system architectures, no dark mode data is available for this computation. For example, in certain architectures all of the ADCs of a certain region of the chip can be dedicated to obtaining only bright mode data during a certain time period. According to certain embodiments, a rolling histogram method may be employed to track an estimate of the bright mode open channel value in situations where other methods fail or produce non-ideal results.

Figure 17:
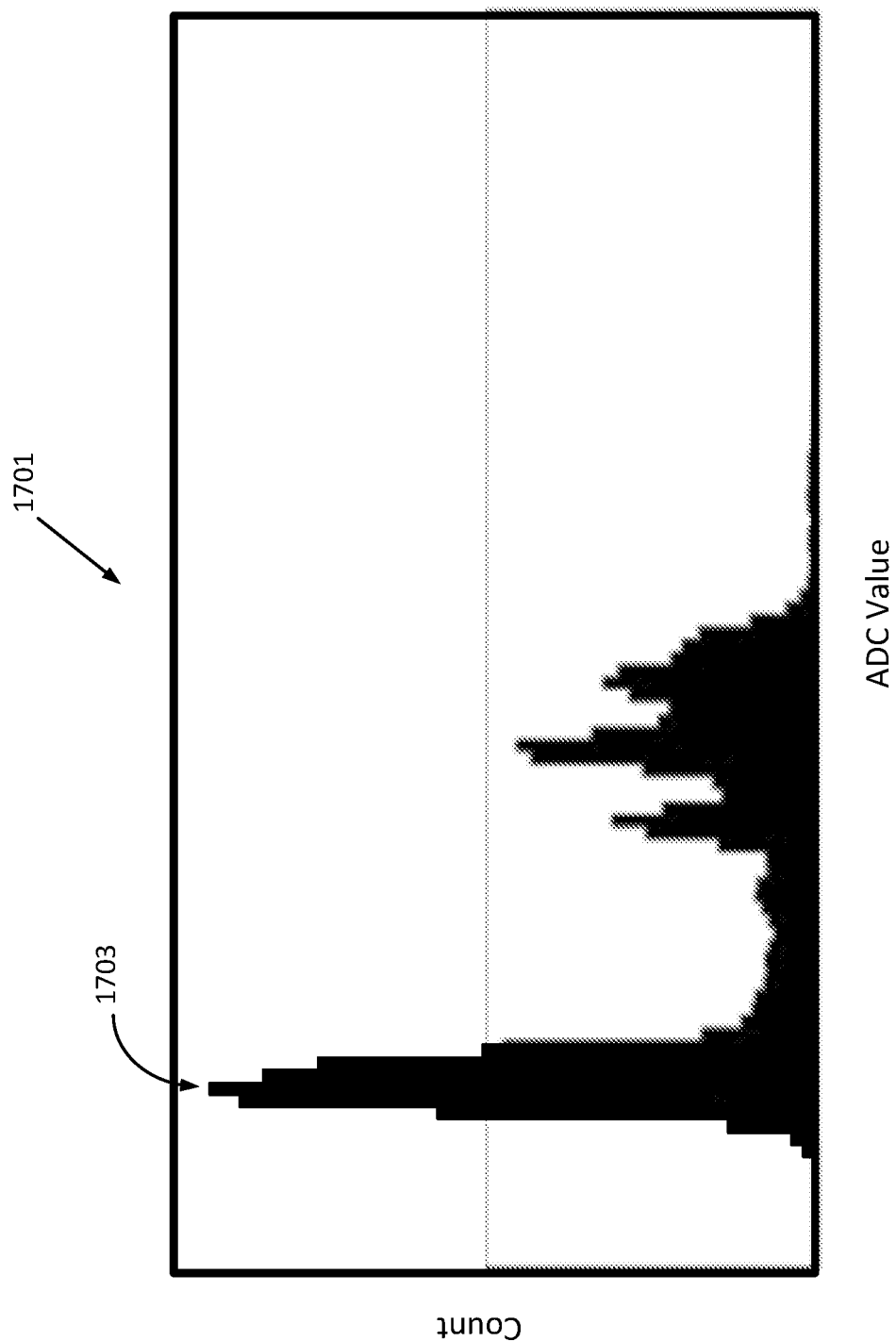
FIG. 17 shows one example running histogram 1701 that can be computed from processed sequencing signal data similar to that shown in FIG. 16B.

FIG. 17 shows one example running histogram 1701 that can be computed from processed sequencing signal data similar to that shown in FIG. 16B. According to certain embodiments, the histogram 1701 can be computed for a population of acquired bright mode data. For example, the data acquired during a window (e.g., ~4 s) of an acquisition run (like that shown in FIG. 14) could be organized into a histogram data structure like histogram 1701. To compute the histogram, bin widths can be chosen to span the dynamic range of the ADC, e.g., the histogram can include 256 bins of unit width corresponding to the ADC values of 0 to 255. As new data points are acquired, the count of the appropriate bin that maps to the acquired ADC value can be updated to keep the histogram updated over time. Once a histogram like histogram 1701 is computed, the open channel voltage can be identified by locating the bin with the largest population in the histogram, e.g., peak 1703.

1. Single Point Running Histogram

To implement a single point "running" histogram, the system can be configured to update the histogram over time by combining one or more newly acquired data points with the historical data according to one or more rules. For example, a histogram can be computed on a rolling basis whereby older data contributes less to any given bin by exponentially downgrading each point's contribution to the total count of the bin based on the age of the data point. For example, consider a bin B(i) that represents the $i^{th}$ bin in the histogram (e.g., the $128^{th}$ bin for ADC values that are equal to 127) and assume that the count of this bin is 1, i.e., it includes one previously measured data point. Further assume that this previously measured data point was acquired during the last acquisition period of the ADC. Now assume that a newly acquired data point also has an ADC value of 127 and therefore should also be added to the same bin as the previous data point. To combine the two data points according to an exponentially decreasing downgrading rule, the current data point is counted as 1 count and the previous data point is counted as some fraction of 1, where the fraction is determined by computing an downgrade coefficient and then weighting the count of the historical data based on the downgrade coefficient.

In some embodiments, an exponential downgrade coefficient such as $$A = e^{-\frac{ndt}{T}}$$

can be employed, where dt is the acquisition period (measured in seconds), n is the age of the data point (the number of acquisition periods that have elapsed since the data point was acquired), and T is an exponential decay parameter that can be chosen based on how quickly to downgrade the contribution of the historical data. In this example, assume that the T=dt for simplicity. Because the historical data point was acquired during the last acquisition cycle, n=1 and therefore $A=e^{-1} \approx 0.37$. Thus, the new bin value would be 1.37 (rather than 2, if no downgrading was used). The simple downgrading example described above can be extended to any number of bins and data sets having any number of data points with associated timestamps. According to certain embodiments, the time constant T for the exponential downgrade in the moving histogram method may be also related to the timescale for the gain change.

2. Iterative Running Histogram

In some embodiments, a running histogram method can be implemented by updating the histogram bin population values $B_t(i)$ according to the following method. First, a histogram is initialized by acquiring data over some predetermined initialization time period $t_{init}$. Then, when a new data point is acquired, it is first determined which histogram bin that new data point belongs in, referred to herein as the active histogram bin k. Next, the population B in the active bin will be updated according to the following recurrence relation $$B_t(k) = \beta * B_{t-1}(k) + (1-\beta)N_e \qquad (28)$$

and the population in the inactive bins, bins having i≠k, will be downgraded according to the following recurrence relation $$B_t(i \neq k) = \beta * B_{t-n1}(i \neq k) \qquad (29)$$

where $0<\beta<1$ is a downgrade coefficient that acts to progressively downgrade the contributions of older histogram data to the updated population. The parameter $N_e$ is referred to herein as the effective number of histogram bins and is chosen to keep the overall population of the histogram approximately constant over the course of a sequencing run. More specifically, without the scaling by $N_e$ in Eqn. (28) the total population in the histogram could decrease over time because the population in bins i≠k will be downgraded according to Eqn. (29). Accordingly, a value for $N_e$ is chosen to counteract this reduction by adding an approximately equal population to the active bin that was removed from the inactive bins as a result of the application of Eqn. (29). In some embodiments, the effective number of bins $N_e$ is set to be the number of bins in the histogram that have non-zero population and could be, e.g., half the total number of bins in the histogram.

The index n is introduced in Eqn. (29) to decouple the update rate of the non-active histogram bins from the data acquisition. For example, in some embodiments, for n=1, both the active histogram bin and the remaining bins are updated every acquisition cycle. Likewise for n=2, the non-active bins are only updated every 2 cycles. Updating the non-active bins only every n acquisition cycles can decreases the overall processing time of the running histogram method.

Employing one of the rolling histogram methods described above for locating and tracking the bright mode open channel value can be more robust than other methods because the methods do not require any dark-channel data and therefore can be used in certain high-throughput modes of the system that have no usable dark channel data. Furthermore, because the method retains historical information in the form of the running histogram, the method can be used to track the open channel level even if minimal and or no open channel data is available, e.g., due to a high rate of threading events. Finally, the rolling histogram method for tracking and estimating the open channel data can be an improvement over other methods such as the use of a Kalman filter because it does not depend on hard coded thresholds to define a range within which the likely open channel value resides. Rather, the open channel can be found based on the data in the histogram itself, e.g., using a peak finding routine. This is possible because the open channel value will often be the largest peak in the histogram, e.g., largest amplitude peak.

In some embodiments, the histogram bin having the largest population (e.g., the largest peak in the histogram) can be taken as the open channel value. Embodiments may further employ a window method that accepts the largest peak only if the largest peak is within an allowed window to avoid tracking threaded levels during long threading events (also referred to as dwell events). In some embodiments, the window width can be dynamically updated to some fraction of the open channel peak in the histogram, e.g., 2.3 times of the full width half max (FWHM).

In the case when the new open channel value is outside the window, a secondary peak (e.g., second largest) is searched between the old open channel peak and the new maximum peak. If the secondary peak is found, meets a peak height requirement, and the secondary peak is within the window, it is accepted as the new OC value. By allowing the secondary peak to possibly serve as the open channel peak, permanent open channel level jumps can be accommodated. This secondary peak search can also ensure that the proper open channel value is tracked even during long dwell events as long as there is some amount of open channel events that also occur during the dwell. Such secondary peak tracking can provide an improvement to address failure rates for open channel when looking at AOC (above open channel) levels, as well as below open channels.

In some embodiments, the input data to the running histogram is processed, e.g., flattened, by a two dimensional transformation as described above. For example, the open channel values $P_{OC}(t_i)$ can be paired with integrated history values $H(t_i)$ and can be processed according to the following equation:

$$P'_{OC}(t_i) = \frac{P_{OC}(t_i) + \rho_{OC} H(t_i)}{1 + \rho_{OC}} \qquad (30)$$

Once the open channel value is determined, that value can be used to normalize the other signal values to ensure that the values for the tag levels are constant in time. For example, a normalization can be applied that divides each threaded signal value by the estimate of the open channel value determined by the running histogram method.

3. Illustrative Flow Chart for Running Histogram Normalization Methods

Figure 18:
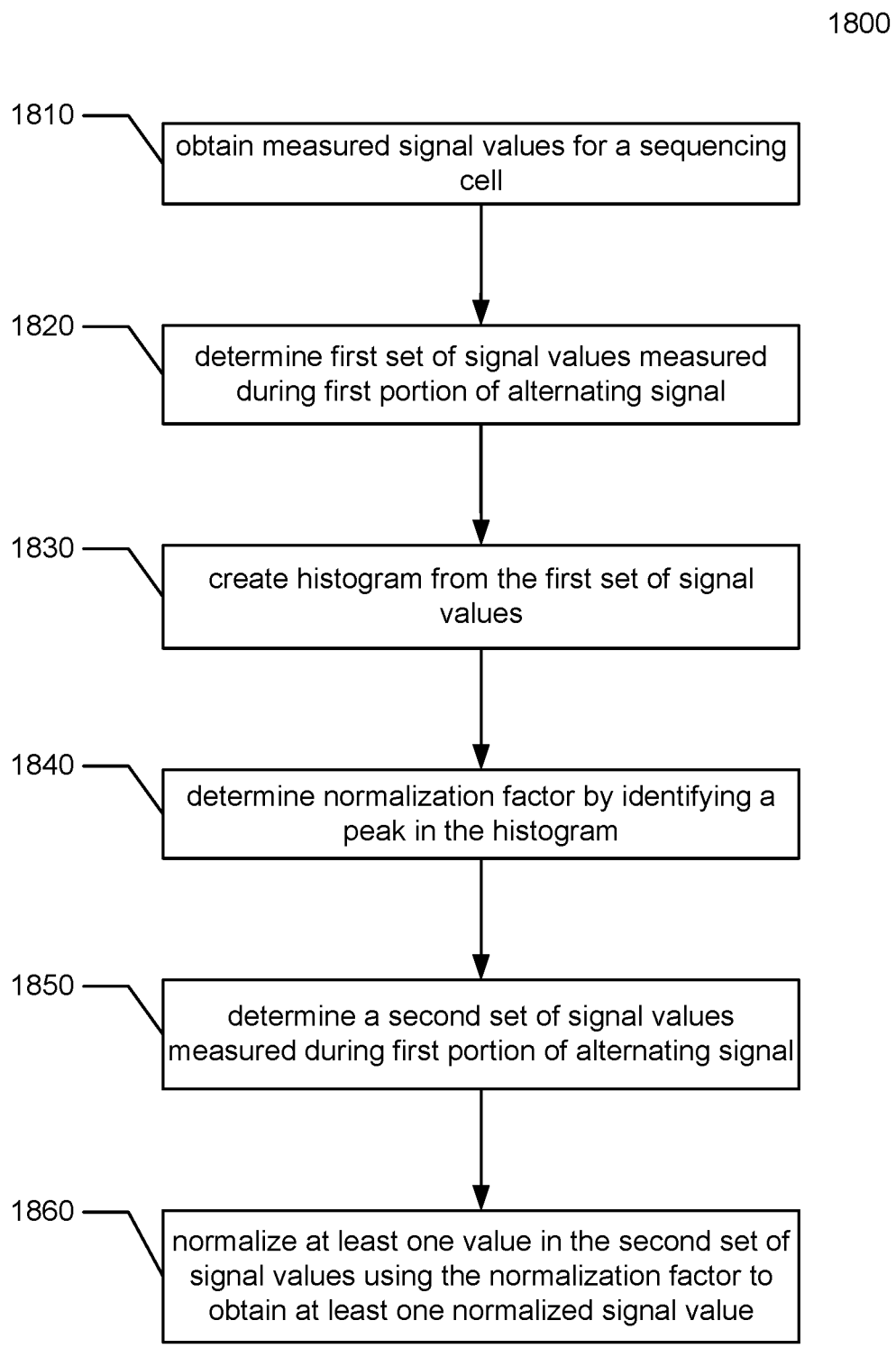
FIG. 18 shows a flow chart that illustrates a method of using a sequencing cell, according to certain embodiments.

FIG. 18 shows a flow chart that illustrates a method of using a sequencing cell, according to certain embodiments. More specifically FIG. 18 describes method for normalization of sequencing signal values using a running histogram as described above in Sections III(C)(1)-(2). In some embodiments, method 1800 may be performed by processor 224 of FIG. 2, digital processor 430, and/or any control logic coupled with the circuits of the sequencing cell.

In step 1810, multiple sequencing signal values $P(t_i)$ are obtained from the sequencing cell. The sequencing signal values can be voltages that are measured by an ADC and sent to a digital processor, e.g., ADC 410 and digital processor 430, as shown in FIG. 4. The digital processor can be part of a computer system that includes other components, e.g., as described in more detail below in reference to FIG. 20. The voltages may correspond to voltages that are measured over one or more bright periods that are themselves over one or more different AC cycles, i.e., it is not required that all the measured data be from the same bright period within a single AC cycle. Such measurements can occur as described herein and can occur at various times of sequencing different parts of a nucleic acid of a given cell. In some cases, the acquired voltages may vary from point to point (even for the same state of the nanopore) due to a variation in the zero point voltage of the cell over time. The applied voltage may be an alternating signal, e.g., an AC signal having a first portion (e.g., a bright period, also referred to herein as a "bright mode") and a second portion (e.g., a dark period, also referred to herein as a "dark mode") relative to a reference voltage. According to certain embodiments, the reference voltage may be a reference voltage (e.g., VPRE 405 in FIG. 4) that is applied to an integrating capacitor, e.g., ncap, as shown in FIG. 4.

In step 1820, a first set of signal values is determined, e.g., one or more voltages measured during the bright period of the alternating signal are selected by the digital processor 430. The first set of voltages may correspond to various bright periods. Such measurements can occur as described herein and can occur at various times of sequencing different parts of a nucleic acid of a given cell. Furthermore, the first set of one or more signal values can correspond to various bright mode threaded channel signal values.

In step 1830, a histogram is created from the first set of signal values, e.g., as described above in Sections III(C)(1)-(2). For example, a histogram (or distribution) of the measured signal can be computed by binning the measured signal values and counting the number of times a particular signal value with a particular ADC count falls within a particular bin.

In step 1840, a normalization factor is determined by identifying a peak in the histogram. According to certain embodiments, neither the peak value, nor the peak width needs to be known in advance of obtaining the measured sequencing signal data in step 1810. For example, a peak detection routine can detect boundaries and characteristics of the peaks, e.g., to identify the largest peak in the histogram. In other embodiments, a second largest peak can be chosen if the signal value of the second largest peak is within a predetermined range of signal values that correspond to the range of acceptable (or likely) open channel signal values (open channel range), e.g., as described in the section above. In some embodiments, the bins at or near the very end of the signal range can be ignored during the initial peak detection routine to avoid edge effects. The signal range for identifying the peak can be established via empirical data from other sequencing runs, cells, chips, etc.

In step 1850, a second set of signal values is determined. Again, as before, the second set of signal values may correspond to various bright periods. Such measurements can occur as described herein and can occur at various times of sequencing different parts of a nucleic acid of a given cell. Furthermore, the second set of one or more signal values can correspond to various bright mode threaded channel signal values.

In step 1860, at least one value in the second set of signal values is normalized using the normalization factor to obtain at least one normalized signal value, e.g., by dividing the at least one value in the second set of signal values by the normalization factor. A plurality of normalized signal values may be obtained.

IV. Normalization and Offset Correction System and Data Flow

Figure 19:
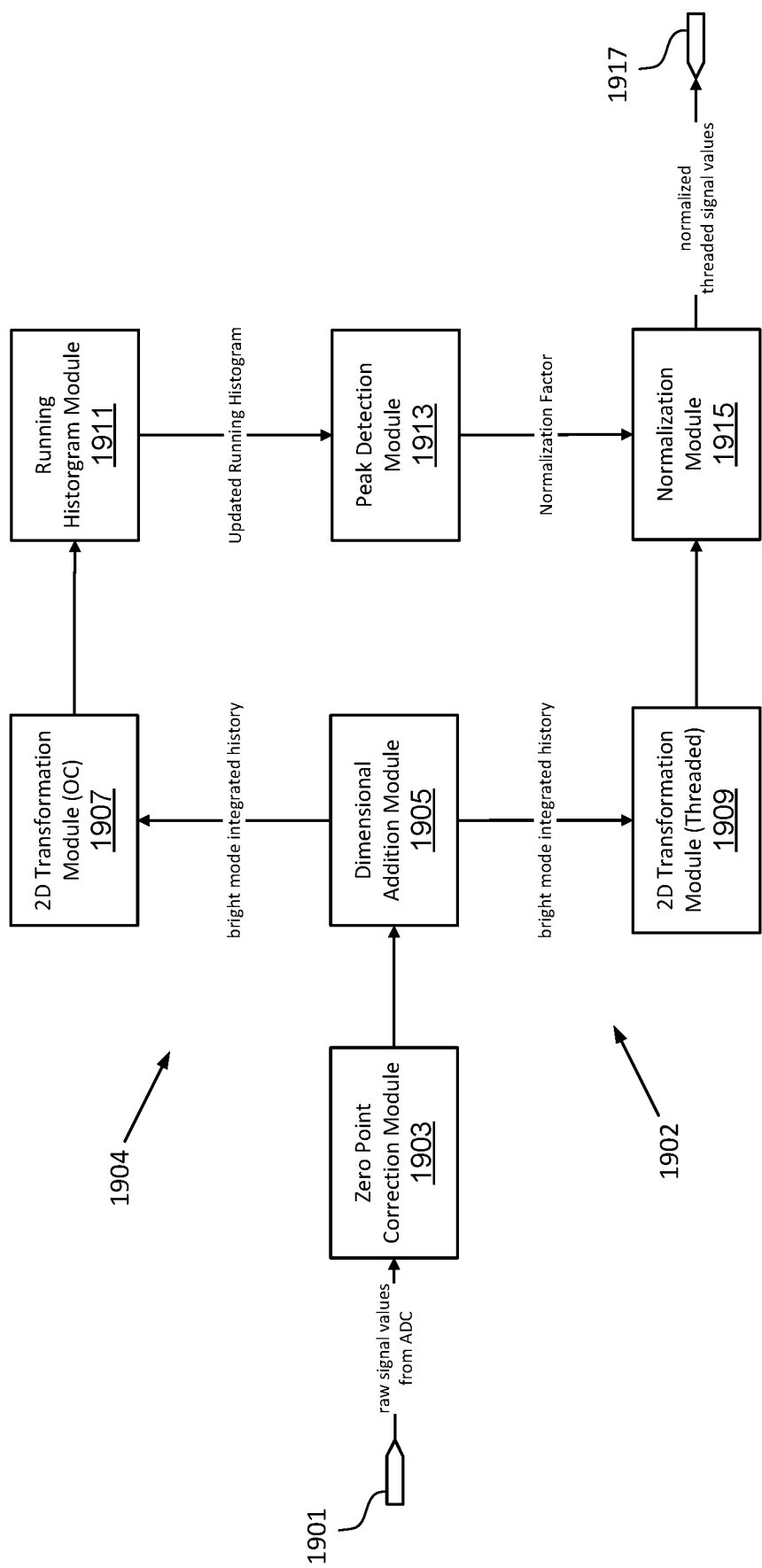
FIG. 19 shows an example system for normalization and offset correction according to some embodiments.

FIG. 19 shows an example system for normalization and offset correction according to some embodiments. More specifically, FIG. 19 illustrates and example of a data flow and logic diagram for a system employing each of the above-described data processing techniques in combination, i.e., the system in FIG. 19 employs zero point correction, baseline shift removal by two-dimensional transformation, and, normalization using a moving histogram. The modules represented in FIG. 19 may be incorporated within a nanopore sequencing system as hardware only software only or a combination of hardware and software, e.g., within one or more computer systems and digital processor of the nanopore sequencing system, e.g., the logic may be implemented within one or more of the nanochip workstation of FIG. 1, processor 224 and memory 226 of FIG. 2, and the digital processor 430 of FIG. 4. In addition, each of the modules shown in FIG. 19 can be operatively connected to one or more computer memories (not shown) such that each module can both access data stored in the one or more computer memories and can save data in the one or more computer memories. Furthermore, each module or the collection of modules can take the form of computer readable instructions or program code that can be executed by one or more processors of a computer system, e.g., the computer system shown in FIG. 20.

A. Correcting for Zero Point Voltage $V_0$

One or more raw sequencing signal values (also referred to herein as "data points") are received from the ADC at input 1901 For example, one or more voltages measured during the bright mode and or dark mode of the applied AC signal, as described above in reference to FIG. 5 above can be received. In the embodiment shown in FIG. 19, the acquired sequencing signal values are first processed zero-point correction module 1903. In some embodiments, the zero-point correction module 1903 can employ a zero-point correction scheme that does not require knowledge of the specific value of $V_0$, e.g., it can subtract corresponding dark mode signal values from the bright mode signal values to remove any effect of a varying zero point voltage $V_0$, as describe above in Section III(C) in reference to FIG. 10. Alternatively, the zero point correction module 1903 can subtract a previously measured value for $V_0$ that has been stored in memory.

The zero point corrected data is then passed to two separate processing flows, a threaded value processing flow 1902 and a normalization factor computation flow 1904. According to certain embodiments, the threaded value processing flow 1902 processes the threaded values by applying a two-dimensional transformation on the threaded values to correct these values for offset shift. According to certain embodiments, the normalization factor computation flow 1904 computes a normalization factor (to be used to correct the threaded values for gain drift) using a moving histogram method.

B. Two-Dimensional Transformation of the Threaded Signal

Turning first to the threaded value processing flow 1902, the data is first processed at the dimensional addition module 1905. The dimensional addition module 1905 can compute a second correlated data point for every acquired bright mode signal value. For example, the dimensional addition module 1905 can pair each bright channel value with a corresponding dark channel value as described above in reference to FIGS. 13A-13C. In some embodiments, dimensional addition module 1905 can perform an integrated history of the bright channel values and then pair each measured bright channel value with a correlated integrated history value, e.g., by implementing the recurrence relation embodied in Eqn. (22), as described above in Section III(B)(2).

After each bright channel data point is converted to a two-dimensional data point by dimensional addition module 1905, the bright channel values and their associated correlated values are sent to two-dimensional transformation module 1909 that applies a two-dimensional transformation to correct for offset drift in the threaded values. According to certain embodiments, two-dimensional transformation module 1909, can take the form of a matrix multiplier that applies a two-dimensional transformation such as rotation or flattening transformation to the each of the two-dimensional data points as described above in Sections III(B)(1)-(3). For example, as shown in FIGS. 14A-14B the two-dimensional transformation can result in clusters of threaded channel data that are rotated/flattened in the 2-dimension space spanning the two-dimensional data points. In other words, the transformed clusters are more horizontal relative to the x-axis in as compared to the unprocessed data. Stated yet another way, the action of the two-dimensional transformation is to reduce the overlap between the five clusters when viewed along the y-dimension. This transformed data is then normalized at by normalization module 1915 where, according to certain embodiments, each value is scaled to (i.e., divided by) an open channel value that was computed in the normalization factor computation flow 1904.

C. Normalization Factor Determination Using Running Histogram

Turning to the normalization factor computation flow 1904, the bright channel values and their associated correlated values are sent to two-dimensional transformation module 1907 that applies a two-dimensional transformation to correct for offset drift in the open channel values. According to certain embodiments, the two-dimensional transformation module 1907 can apply a transformation in the form of a matrix multiplication to the each of the two-dimensional data points. The transformation applied by the two-dimensional transformation module 1907 can result in the variance of the open channel data being reduced in one dimension, similar to how the variance of the threaded channel data was reduced by the two-dimensional transformation described above in reference to the threaded value processing flow 1902. The transformed open channel signal values are then sent to running histogram module 1911 where an updated running histogram (i.e., a population distribution) of the data is computed based off the new data and historical data that is stored in memory.

According to certain embodiments, the updated running histogram can be computed from the historical data in a number of ways as described above in reference to Section III(C). For example, the contribution of the historical data to the running histogram can be downgraded based on age. Once the newly acquired data is combined with the historical data to form an updated running histogram, the peak detection module 1913 executes a peak finding routine to locate the largest peak in the histogram (i.e., the most populous value in the sequence signal data) and then selects the corresponding signal value as the best estimate of the open channel signal value to be used as the normalization factor. The normalization factor determined by this method results in an improved estimate of the open channel voltage value, even when the most recent measurement may not include any open channel values.

Returning to the threaded value processing flow 1902, the transformed threaded data output by the 2D transformation module 1909 is normalized using the normalization factor resulting in the normalized threaded signal that is output at output node 1917, e.g., using Eqn. (5) or Eqn. (26) The threaded values are not only more horizontal (i.e. the variation in the bright channel values is smaller within each cluster of the threaded values) but the data is also scaled such that the dynamic range is approximately between 0 and 1. As a result, the processing system described herein results in threaded values (i.e., tag values) that are more easily distinguished from one another and also values that are more stable in over time because the effects of both gain drift and offset shift have been minimized.

V. Computer System

Figure 20:
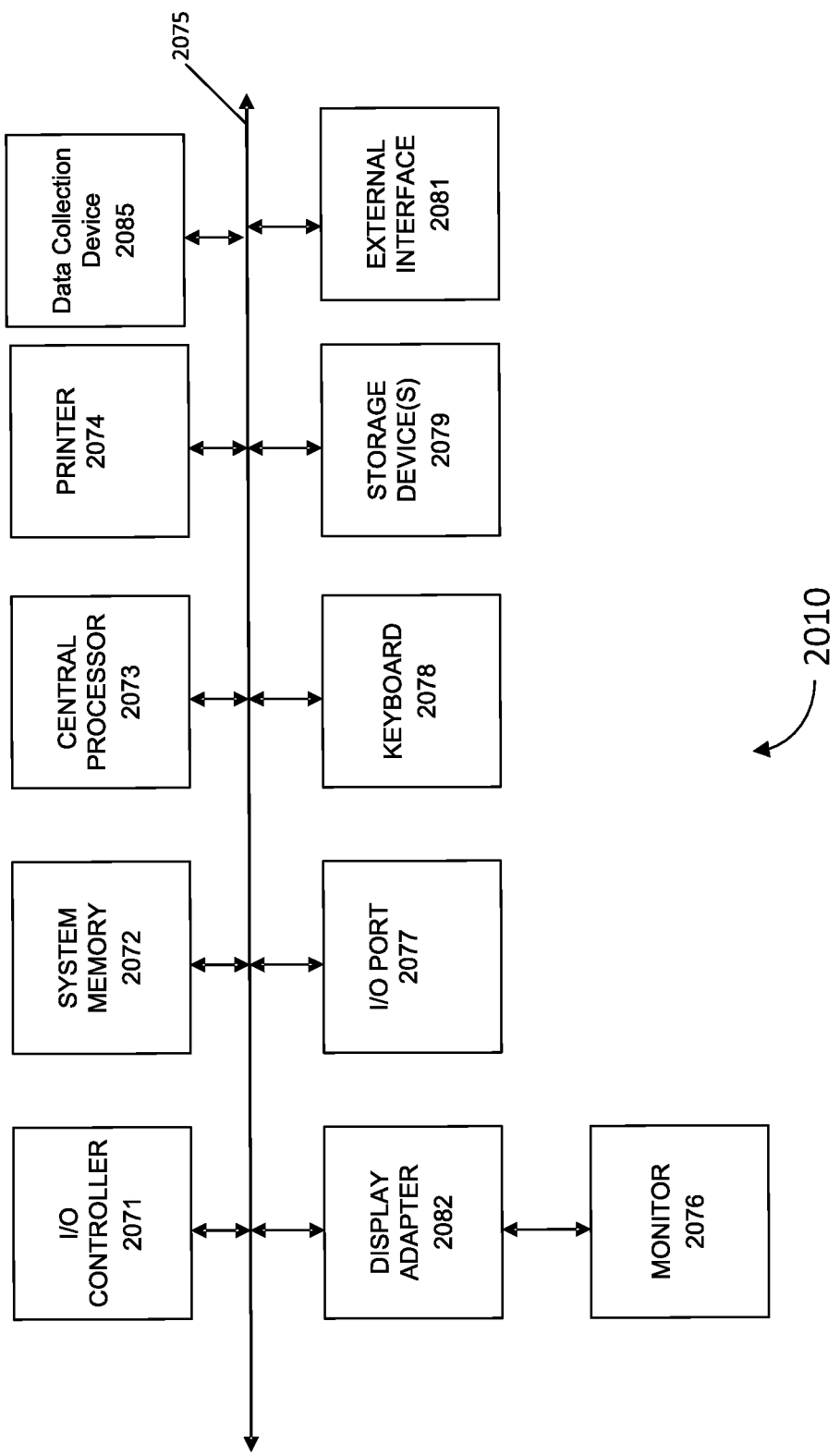
FIG. 20 is a computer system, according to certain aspects of the present disclosure.

Any of the computer systems mentioned herein may utilize any suitable number of subsystems. Examples of such subsystems are shown in FIG. 20 in computer system 2010. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 20 are interconnected via a system bus 2075. Additional subsystems such as a printer 2074, keyboard 2078, storage device(s) 2079, monitor 2076, which is coupled to display adapter 2082, and others are shown. Peripherals and input/output (I/O) devices, which couple to I/O controller 2071, can be connected to the computer system by any number of means known in the art such as input/output (I/O) port 2077 (e.g., USB, FireWire). For example, I/O port 2077 or external interface 2081 (e.g. Ethernet, Wi-Fi, etc.) can be used to connect computer system 2010 to a wide area network such as the Internet, a mouse input device, or a scanner. The interconnection via system bus 2075 allows the central processor 2073 to communicate with each subsystem and to control the execution of a plurality of instructions from system memory 2072 or the storage device(s) 2079 (e.g., a fixed disk, such as a hard drive, or optical disk), as well as the exchange of information between subsystems. The system memory 2072 and/or the storage device(s) 2079 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 2081 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A method of using a sequencing cell, the method comprising:
    applying a voltage across the sequencing cell, the sequencing cell including a nucleic acid, wherein the applied voltage includes an alternating signal having a first portion and a second portion relative to a reference voltage;
    acquiring, during the first portion of the alternating signal, a plurality of signal values from the sequencing cell, wherein during the first portion of the alternating signal a tag molecule is threaded in a nanopore of the sequencing cell, the tag molecule corresponding to a particular nucleotide, wherein the signal value varies over time;
    acquiring a plurality of correlated signal values that are correlated with respective values of the plurality of acquired signal values thereby forming a plurality of two-dimensional data points, wherein the plurality of two-dimensional data points comprise values in a first dimension that equal the plurality of acquired signal value and values in a second dimension that equal the plurality of correlated signal values, wherein the plurality of correlated signal values are a plurality of acquired signal values that are acquired during the second portion of the alternating signal, wherein during the second portion of the alternating signal, no tag molecule is threaded in the nanopore of the sequencing cell; and
    computing a plurality of transformed signal values by applying a two-dimensional transformation to the plurality of two-dimensional data points, wherein the two-dimensional transformation compensates for a variation of the acquired signal value.

2. The method of claim 1, wherein the plurality of correlated signal values are determined by computing a plurality of integrated histories of a plurality of acquired voltages.

3. The method of claim 1, wherein the two-dimensional transformation is a matrix multiplication.

4. A method of using a sequencing cell, the method comprising:
    applying a voltage across the sequencing cell, the sequencing cell including a nucleic acid, wherein the applied voltage includes an alternating signal having a first portion and a second portion relative to a reference voltage;
    acquiring, during the first portion of the alternating signal, a plurality of signal values from the sequencing cell, wherein during the first portion of the alternating signal a tag molecule is threaded in a nanopore of the sequencing cell, the tag molecule corresponding to a particular nucleotide, wherein the signal value varies over time;
    acquiring a plurality of correlated signal values that are correlated with respective values of the plurality of acquired signal values thereby forming a plurality of two-dimensional data points, wherein the plurality of two-dimensional data points comprise values in a first dimension that equal the plurality of acquired signal value and values in a second dimension that equal the plurality of correlated signal values;
    computing a plurality of transformed signal values by applying a two-dimensional transformation to the plurality of two-dimensional data points, wherein the two-dimensional transformation compensates for a variation of the acquired signal value;
    computing a normalization factor based on a histogram of the plurality of transformed signal values;
    normalizing the plurality of transformed signal values using the normalization factor to obtain a plurality of normalized signal values; and
    identifying one or more states of the nanopore based on the plurality of normalized signal values.

5. The method of claim 4, wherein the normalization factor is determined to be an acquired signal value having a largest amplitude peak in the histogram of the plurality of transformed signal values.

6. The method of claim 5, further comprising, normalizing at least one transformed signal value of the plurality of transformed signal values by dividing the at least one transformed signal value by the normalization factor.

7. A method of using a sequencing cell, the method comprising:
applying a voltage across the sequencing cell, the sequencing cell including a nucleic acid, wherein the applied voltage includes an alternating signal having a first portion and a second portion relative to a reference voltage;
acquiring, during the first portion of the alternating signal, a plurality of signal values from the sequencing cell, wherein during the first portion of the alternating signal a tag molecule is threaded in a nanopore of the sequencing cell, the tag molecule corresponding to a particular nucleotide, wherein the signal value varies over time;
acquiring a plurality of correlated signal values that are correlated with respective values of the plurality of acquired signal values thereby forming a plurality of two-dimensional data points, wherein the plurality of two-dimensional data points comprise values in a first dimension that equal the plurality of acquired signal value and values in a second dimension that equal the plurality of correlated signal values;
computing a plurality of transformed signal values by applying a two-dimensional transformation to the plurality of two-dimensional data points, wherein the two-dimensional transformation compensates for a variation of the acquired signal value; and
determining the two-dimensional transformation to be the transformation that reduces the variation of the plurality of signal values, wherein the two-dimensional transformation is applied to the plurality of two-dimensional data points and wherein the two-dimensional transformation compensates for the voltage offset shift of the cell.

8. A method of using a sequencing cell, the method comprising:
obtaining a plurality of measured signal values for a sequencing cell having a voltage applied across the sequencing cell, the cell including a nucleic acid, wherein the applied voltage includes an alternating signal having a first portion and a second portion relative to a reference voltage;
determining a first set of signal values measured during the first portion of the alternating signal;
creating a histogram from the first set of signal values;
determining a normalization factor by identifying a peak in the histogram, wherein the peak corresponds to an open channel signal value of the sequencing cell;
determining a second set of signal values measured during the first portion of the alternating signal; and
normalizing at least one value in the second set of signal values using the normalization factor to obtain at least one normalized signal value;
wherein identifying the peak in the histogram comprises choosing a second largest amplitude peak to be the peak that corresponds to the open channel signal value of the sequencing cell when a signal value of the second largest amplitude peak is within a range of signal values that define an open channel range and a signal value of the largest amplitude peak is outside the range of signal values.

9. The method of claim 8, wherein identifying the peak in the histogram comprises choosing a largest amplitude peak to be the peak that corresponds to the open channel signal value of the sequencing cell.

10. A method of using a sequencing cell, the method comprising:
obtaining a plurality of measured signal values for a sequencing cell having a voltage applied across the sequencing cell, the cell including a nucleic acid, wherein the applied voltage includes an alternating signal having a first portion and a second portion relative to a reference voltage;
determining a first set of signal values measured during the first portion of the alternating signal;
creating a histogram from the first set of signal values;
determining a normalization factor by identifying a peak in the histogram, wherein the peak corresponds to an open channel signal value of the sequencing cell;
determining a second set of signal values measured during the first portion of the alternating signal; and
normalizing at least one value in the second set of signal values using the normalization factor to obtain at least one normalized signal value;
wherein creating a histogram from the first set of signal values comprises, for each point of the first set of signal values, discounting a contribution of each point to the histogram based on an age of each point.

11. A method of using a sequencing cell, the method comprising:
obtaining a plurality of measured signal values for a sequencing cell having a voltage applied across the sequencing cell, the cell including a nucleic acid, wherein the applied voltage includes an alternating signal having a first portion and a second portion relative to a reference voltage;
determining a first set of signal values measured during the first portion of the alternating signal;
creating a histogram from the first set of signal values;
determining a normalization factor by identifying a peak in the histogram, wherein the peak corresponds to an open channel signal value of the sequencing cell;
determining a second set of signal values measured during the first portion of the alternating signal; and
normalizing at least one value in the second set of signal values using the normalization factor to obtain at least one normalized signal value;
before creating the histogram, obtaining a first set of correlated signal values that are correlated with the first set of signal values measured during the first portion of the alternating signal thereby forming a set of two-dimensional data points;
determining a set of transformed signal values based on the set of two-dimensional data points, wherein the transformed signal value is computed by applying a two-dimensional transformation to the set of two-dimensional data points; and
using the a set of transformed signal values to create the histogram.

12. A method of using a sequencing cell, the method comprising:
obtaining a plurality of measured signal values for a sequencing cell having a voltage applied across the sequencing cell, the cell including a nucleic acid, wherein the applied voltage includes an alternating signal having a first portion and a second portion relative to a reference voltage;
determining a first set of one or more signal values measured during the first portion of the alternating signal, when a tag molecule is threaded in a nanopore of the sequencing cell, the tag molecule corresponding to a particular nucleotide;

determining a second set of one or more signal values measured during the first portion of the alternating signal, when the tag molecule is not threaded in the nanopore of the sequencing cell;

determining a third set of one or more signal values measured during the second portion of the alternating signal when the tag molecule is not threaded in the nanopore of the sequencing cell;

subtracting, from the first set of one or more signal values, corresponding values of the third set of one or more signal values thereby generating a first set of one or more zero point compensated signal values; and subtracting, from the second set of one or more signal values, corresponding values of the third set of one or more signal values to generate a second set of one or more zero point compensated signal values.

13. The method of claim 12, further comprising:

determining corresponding correlated signal values that correspond to the first and second sets of one or more zero point compensated signal values, thereby forming a plurality of two-dimensional data points; and applying a two-dimensional transformation to reduce a variation of the first set of one or more zero point compensated signal values.

14. The method of claim 12, further comprising:

creating a histogram from the first and second sets of one or more zero point compensated signal values;

determining a normalization factor by identifying a peak in the histogram, wherein the peak corresponds to an open channel signal value of the sequencing cell; and normalizing the first set of one or more zero point compensated signal values by dividing by the normalization factor.

15. The method of claim 12, wherein at least one signal value of the second set of one or more zero point compensated signal values is determined to be a normalization factor for normalizing at least one signal value of the first set of one or more zero point compensated signal values.

* * * * *